(12) United States Patent
Melius et al.

(10) Patent No.: US 6,802,834 B2
(45) Date of Patent: Oct. 12, 2004

(54) ABSORBENT ARTICLE HAVING DISCONTINUOUS ABSORBENT CORE

(75) Inventors: Shannon K. Melius, Appleton, WI (US); Eric D. Johnson, Larsen, WI (US); Paul E. Olmstead, Menasha, WI (US); Michael B. Venturino, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 36 days.

(21) Appl. No.: 10/306,185

(22) Filed: Nov. 27, 2002

(65) Prior Publication Data

US 2003/0139721 A1 Jul. 24, 2003

Related U.S. Application Data

(60) Provisional application No. 60/350,079, filed on Jan. 15, 2002.

(51) Int. Cl.[7] ................................................ A61F 13/15
(52) U.S. Cl. .................................. 604/385.31; 604/378
(58) Field of Search ....................... 604/385.01, 385.31, 604/378, 382

(56) References Cited

U.S. PATENT DOCUMENTS

| | | | |
|---|---|---|---|
| 3,085,309 A | 4/1963 | Olson | |
| 3,156,751 A | 11/1964 | Valdes et al. | |
| 3,587,579 A | 6/1971 | Sabee | |

(List continued on next page.)

FOREIGN PATENT DOCUMENTS

| | | |
|---|---|---|
| DE | 198 23 954 A1 | 12/1999 |
| EP | 0 151 018 A2 | 8/1985 |
| EP | 0 226 939 A2 | 12/1986 |
| EP | 0 297 180 B1 | 1/1989 |
| EP | 0 298 348 A1 | 11/1989 |
| EP | 0 399 511 A2 | 11/1990 |
| EP | 0 467 409 A1 | 1/1992 |
| GB | 2168612 A | 6/1986 |
| JP | 09122172 | 5/1997 |
| JP | 10211236 | 8/1998 |
| WO | WO 93/18729 A1 | 9/1993 |
| WO | WO 96/00550 A1 | 1/1996 |
| WO | WO 99/22685 A1 | 5/1999 |
| WO | WO 99/25281 A1 | 5/1999 |
| WO | WO 00/10498 A1 | 3/2000 |
| WO | WO 00/37725 A1 | 6/2000 |
| WO | WO 00/63479 A1 | 10/2000 |
| WO | WO 01/92003 A1 | 12/2001 |
| WO | WO 03/059232 A2 | 7/2003 |

OTHER PUBLICATIONS

International Search Report, dated May 28, 2003 in PCT/US 03/00881, 8 pages.
International Search Report for PCT/US 03/16480 dated Oct. 13, 2003, 5 pages.
International Search Report for PCT/US 03/01337 dated Jul. 21, 2003.
International Search Report for PCT/US 03/00293 dated Jul. 29, 2003.

Primary Examiner—John J. Calvert
Assistant Examiner—Michael G. Bogart
(74) Attorney, Agent, or Firm—Senniger Powers

(57) ABSTRACT

An absorbent article is constructed with a discontinuous absorbent core strengthened by a reinforcing scrim material embedded in the absorbent material of the core. The scrim facilitates maintenance of the integrity of the core in use although the core may be weakened by the provision of ventilation openings or other discontinuities. The scrim also helps to keep the proper location of the absorbent core within the article. Moreover, use of scrim or other reinforcing material facilitates the manufacture of the absorbent core and of the absorbent article.

41 Claims, 19 Drawing Sheets

U.S. PATENT DOCUMENTS

| | | |
|---|---|---|
| 3,683,921 A | 8/1972 | Brooks et al. |
| 3,816,231 A | 6/1974 | Marshall |
| 3,856,012 A | 12/1974 | MacDonald et al. |
| 3,862,877 A | 1/1975 | Camden |
| 3,867,935 A | 2/1975 | Eisdorfer et al. |
| 3,888,248 A | 6/1975 | Moore et al. |
| 3,935,979 A | 2/1976 | Hickey |
| 4,001,472 A | 1/1977 | Thomas et al. |
| 4,028,455 A | 6/1977 | Ueda et al. |
| 4,141,772 A | 2/1979 | Buell |
| 4,217,078 A | 8/1980 | Buell |
| 4,235,237 A | 11/1980 | Mesek et al. |
| 4,303,189 A | 12/1981 | Wiley et al. |
| 4,392,862 A | 7/1983 | Marsan et al. |
| 4,425,127 A | 1/1984 | Suzuki et al. |
| 4,666,647 A | 5/1987 | Enloe et al. |
| 4,674,966 A | 6/1987 | Johnson et al. |
| 4,704,112 A | 11/1987 | Suzuki et al. |
| 4,710,185 A | 12/1987 | Sneyd, Jr. et al. |
| 4,761,258 A | 8/1988 | Enloe |
| 4,764,325 A | 8/1988 | Angstadt |
| 4,765,780 A | 8/1988 | Angstadt |
| 4,773,903 A | 9/1988 | Weisman et al. |
| 4,775,579 A | 10/1988 | Hagy et al. |
| 4,810,568 A | 3/1989 | Buyofsky et al. |
| 4,837,715 A | 6/1989 | Ungpiyakul et al. |
| 4,904,440 A | 2/1990 | Angstadt |
| 4,908,175 A | 3/1990 | Angstadt |
| 4,915,897 A | 4/1990 | Farrington et al. |
| 4,927,346 A | 5/1990 | Kaiser et al. |
| 4,927,582 A | 5/1990 | Bryson |
| 5,004,579 A | 4/1991 | Wislinski et al. |
| 5,017,324 A | 5/1991 | Kaiser et al. |
| 5,124,188 A | 6/1992 | Roe et al. |
| 5,128,082 A | 7/1992 | Makoui |
| 5,139,841 A | 8/1992 | Makoui et al. |
| 5,144,729 A | 9/1992 | Austin et al. |
| 5,161,283 A | 11/1992 | Hansen |
| 5,219,633 A | 6/1993 | Sabee |
| 5,281,208 A | 1/1994 | Thompson et al. |
| 5,302,445 A | 4/1994 | DePetris et al. |
| 5,328,072 A | 7/1994 | Ruessmann et al. |
| 5,389,095 A | 2/1995 | Suzuki et al. |
| 5,389,202 A | 2/1995 | Everhart et al. |
| 5,429,788 A | 7/1995 | Ribble et al. |
| 5,447,677 A | 9/1995 | Griffoul et al. |
| 5,466,409 A | 11/1995 | Partridge et al. |
| 5,486,167 A | 1/1996 | Dragoo et al. |
| 5,505,720 A | 4/1996 | Walters et al. |
| 5,527,300 A | 6/1996 | Sauer |
| 5,531,729 A | 7/1996 | Coles et al. |
| 5,591,148 A | 1/1997 | McFall et al. |
| 5,607,415 A | 3/1997 | Datta et al. |
| 5,614,283 A | 3/1997 | Potnis et al. |
| 5,672,306 A | 9/1997 | Sprang et al. |
| 5,704,931 A | 1/1998 | Holtman et al. |
| 5,756,039 A | 5/1998 | McFall et al. |
| 5,762,844 A | 6/1998 | Van Himbergen et al. |
| 5,772,813 A | 6/1998 | Bitowft et al. |
| 5,803,334 A | 9/1998 | Patel et al. |
| 5,818,719 A | 10/1998 | Brandon et al. |
| 5,866,173 A | 2/1999 | Reiter et al. |
| 5,871,613 A | 2/1999 | Bost et al. |
| 5,873,963 A | 2/1999 | Trombetta et al. |
| 5,902,757 A | 5/1999 | Stern et al. |
| 5,916,661 A | 6/1999 | Benson et al. |
| 5,925,439 A | 7/1999 | Haubach |
| 5,938,648 A | 8/1999 | LaVon et al. |
| 5,944,706 A | 8/1999 | Palumbo et al. |
| 5,947,945 A | 9/1999 | Cree et al. |
| 5,961,509 A | 10/1999 | Kling |
| 5,997,520 A | 12/1999 | Ahr et al. |
| 6,048,489 A | 4/2000 | Reiter et al. |
| 6,060,637 A | 5/2000 | Bitowft et al. |
| 6,107,538 A | 8/2000 | Young et al. |
| 6,203,654 B1 | 3/2001 | McFall et al. |
| 6,220,999 B1 | 4/2001 | Kugler et al. |
| 6,258,996 B1 | 7/2001 | Goldman |
| 6,262,331 B1 | 7/2001 | Nakahata et al. |
| 6,284,943 B1 * | 9/2001 | Osborn et al. ............. 604/366 |
| 6,296,862 B1 | 10/2001 | Paul et al. |
| 6,330,735 B1 | 12/2001 | Hahn et al. |
| 6,375,644 B2 | 4/2002 | Mizutani |
| 6,416,697 B1 | 7/2002 | Venturino et al. |
| 6,492,574 B1 * | 12/2002 | Chen et al. ................ 604/378 |
| 6,533,978 B1 | 3/2003 | Wisneski et al. |
| 6,533,989 B1 | 3/2003 | Wisneski et al. |
| 6,630,096 B2 | 10/2003 | Venturino et al. |
| 2001/0039405 A1 * | 11/2001 | Keuhn et al. ............... 604/360 |
| 2003/0116888 A1 | 6/2003 | Rymer et al. |
| 2003/0119401 A1 | 6/2003 | Chakravarty et al. |
| 2003/0132556 A1 | 7/2003 | Venturino et al. |
| 2003/0139721 A1 | 7/2003 | Melius et al. |
| 2004/0102752 A1 * | 5/2004 | Chen et al. ................ 604/378 |

* cited by examiner

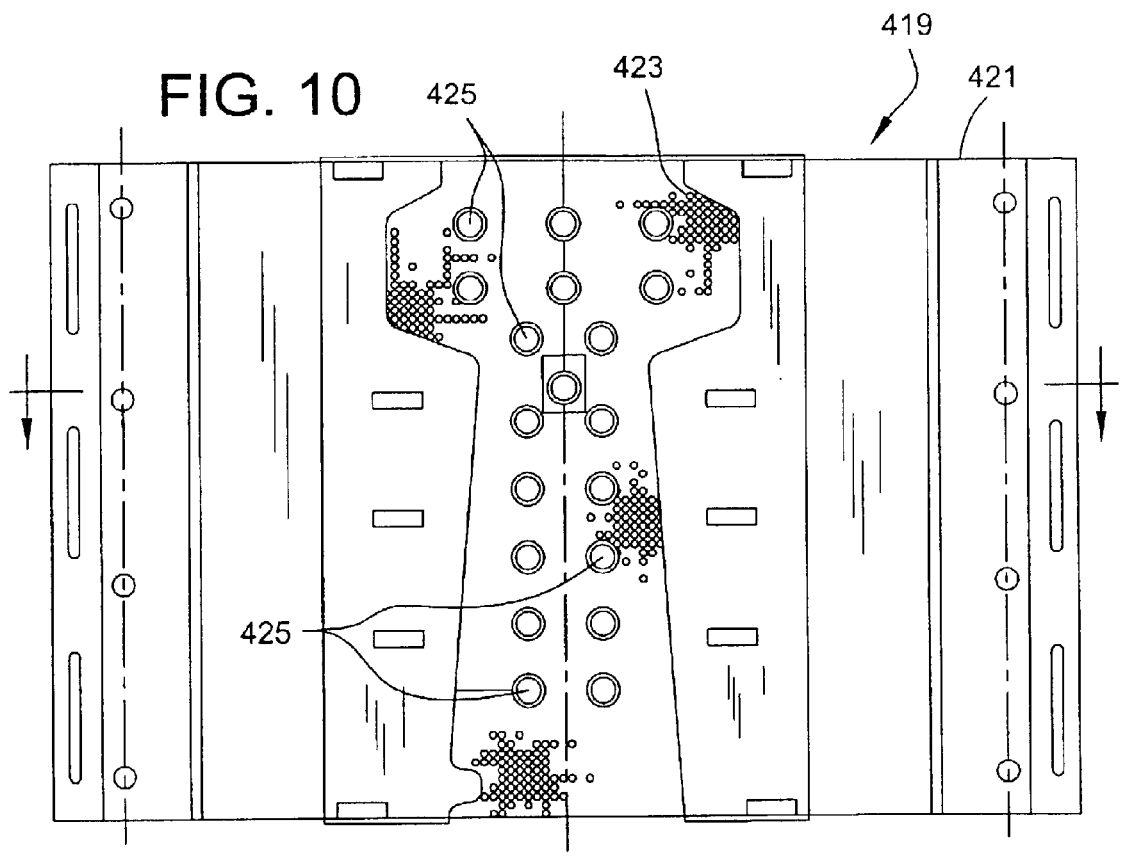
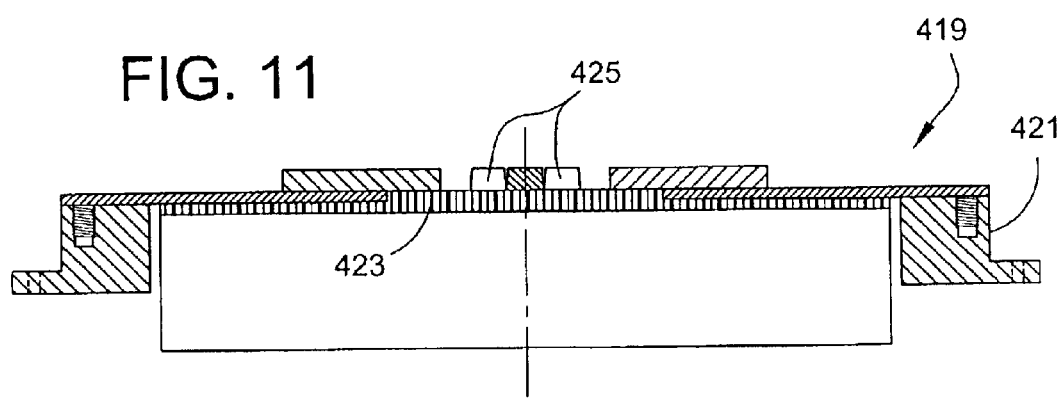

ABSORBENT ARTICLE HAVING DISCONTINUOUS ABSORBENT CORE

REFERENCE TO RELATED APPLICATIONS

This application claims benefit to U.S. provisional application Ser. No. 60/350,079, filed Jan. 15, 2002, entitled "Scrim Reinforced Absorbent."

BACKGROUND OF INVENTION

This invention generally relates to an absorbent article and an absorbent structure for such an article. The absorbent structure has an absorbent core which is formed so as to provide one or more passages facilitating the flow of air through the absorbent core for ventilation of the skin. The absorbent structure can be employed in absorbent articles, such as disposable diapers, child's training pants, feminine care articles, incontinence articles, bandages and the like.

Absorbent structures, such as for disposable absorbent garments, may include absorbent cores conventionally formed by air forming or air laying techniques. For example, the manufacture of the absorbent core may begin by fiberizing a fibrous sheet of cellulosic or other suitable absorbent material in a conventional fiberizer, or other shredding or comminuting device, to form discrete fibers. Particles of superabsorbent material are mixed with the discrete fibers. The fibers and superabsorbent particles are then entrained in an air stream and directed to a foraminous forming surface upon which the fibers and superabsorbent particles are deposited to form an absorbent fibrous web. As used herein, "absorbent material" may include both fibrous material and superabsorbent material.

In addition, bonding agents or other strengthening components (e.g., heat set staple binder fibers) may be incorporated to provide a more stabilized web. Other techniques have also been employed to form webs of stabilized absorbent material. Such techniques include dry-forming techniques, wet-laying techniques, foam-forming techniques, and various wet-forming techniques. The resulting webs of absorbent material include absorbent fibers, natural fibers, synthetic fibers, superabsorbent materials, binders, and strengthening components in desired combinations. However formed, the absorbent web may then be stored or immediately directed for further processing (e.g., being cut into individual absorbent cores) and assembly with other components to produce a final absorbent article.

In order to improve the ventilation of the portion of the wearer's body covered by an absorbent article, it is known to provide openings in the absorbent core or other discontinuities of the absorbent core, such as forming the core of distinct, spaced apart sections. While openings in the absorbent core improve ventilation and skin health for the wearer, they also provide sites for the formation and propagation of cracks and tears in the absorbent material of the core resulting in loss of core integrity. As the absorbent core becomes loaded with urine (or other exudates) and/or under loads applied to the core as the wearer moves, the absorbent core may bunch up in certain locations and/or tear apart into several distinct clumps. This phenomenon reduces the effectiveness of the absorbent core to absorb additional fluid insults, and adversely affects fit. An absorbent garment having a bunched and/or broken apart absorbent core may sag and gap. Sagging reduces fit and comfort, while gapping can result in leaking.

Automated manufacture of absorbent articles including absorbent cores which are apertured or defined by completely separate core sections presents certain challenges. In one conventional form of manufacturing, the absorbent core (sections) are air formed by the deposition of fibers and/or other absorbent material on a rotating drum. Difficulty arises in removing the formed absorbent core from the drum. Apertured absorbent cores may tear apart under the forces required to peel the cores from the drum. Where the core is formed from smaller, unconnected sections, it can be difficult to successfully capture the leading edge of each successive section on the drum (e.g., as by applying a vacuum) to peel the section from the drum. After the core sections are removed from the drum, control of the sections is more difficult to maintain, potentially resulting in misalignment of the core sections in the assembled absorbent article, or even complete omission of a core section causing the absorbent article to be rejected.

Another problem associated with absorbent cores made up of distinct, separated sections is the maintenance of the relative position of the sections in the finished absorbent article. Sections of an absorbent core may more readily move relative to one another in use. In addition to being aesthetically unpleasing, this lack of integrity or loss of position can have an impact on product performance by breaking up the absorbent core or dislocating the core so that it is not properly positioned to receive liquid. These problems can lead to loss of fluid control, liquid handling and wicking which can contribute to leaking.

SUMMARY OF THE INVENTION

An absorbent article has a discontinuous absorbent core which is reinforced to hold its position and configuration, as well as to inhibit tearing and breakage of the absorbent material in both manufacture and use. In a particular aspect, the absorbent structure can include a matrix of absorbent fibers formed to have discontinuities, but reinforced with a reinforcing member embedded in the fibrous matrix. In another form, the absorbent core has distinct sections which are held in position by an interconnecting reinforcing member. By incorporating the various aspects and features into desired configurations, the present invention can provide an article that more effectively incorporates a reinforced absorbent structure. An article of the present invention has a high-strength absorbent structure that provides reduced irritation to the wearer along with improved skin health, and can be constructed at reduced cost.

In one aspect, an absorbent structure for absorbing liquid in an absorbent article comprises an absorbent member made at least in part of an absorbent material. The absorbent member has at least one zone therein having a higher air permeability than an adjacent lower air permeability zone of the absorbent member. A reinforcing member at least partially embedded in the absorbent member reinforces the absorbent member to hold its configuration under loads experienced by the absorbent structure.

In another aspect of the present invention, an absorbent article adapted to be worn by a wearer for absorbing body exudates comprises a liquid permeable liner and a backsheet layer. The article further includes an absorbent structure as set forth in the preceding paragraph.

In a further aspect of the invention, an absorbent structure for absorbing liquid in an absorbent article comprises an absorbent member made at least in part of an absorbent material. The absorbent member has at least one void defined therein and at least some absorbent material of the absorbent material is spaced apart across the void. A reinforcing member at least partially embedded in the absorbent member reinforces the absorbent member to maintain its integrity under loads experienced by the absorbent structure.

Other features of the invention will be in part apparent and in part pointed out hereinafter.

BRIEF DESCRIPTION OF THE DRAWINGS

FIG. 10 is a top plan view of a forming screen for making the absorbent structure of FIG. 6A;

FIG. 11 is an end elevation of the forming screen;

Corresponding reference characters indicate corresponding parts throughout the several views of the drawings.

DETAILED DESCRIPTION OF THE DRAWINGS

The technology of the invention can be used to produce various types of desired absorbent articles. Such articles can include, for example, infant diapers, children's training pants, feminine care articles, adult incontinence garments, bandages and the like. The articles may be disposable, and intended for limited use.

Figure 1:
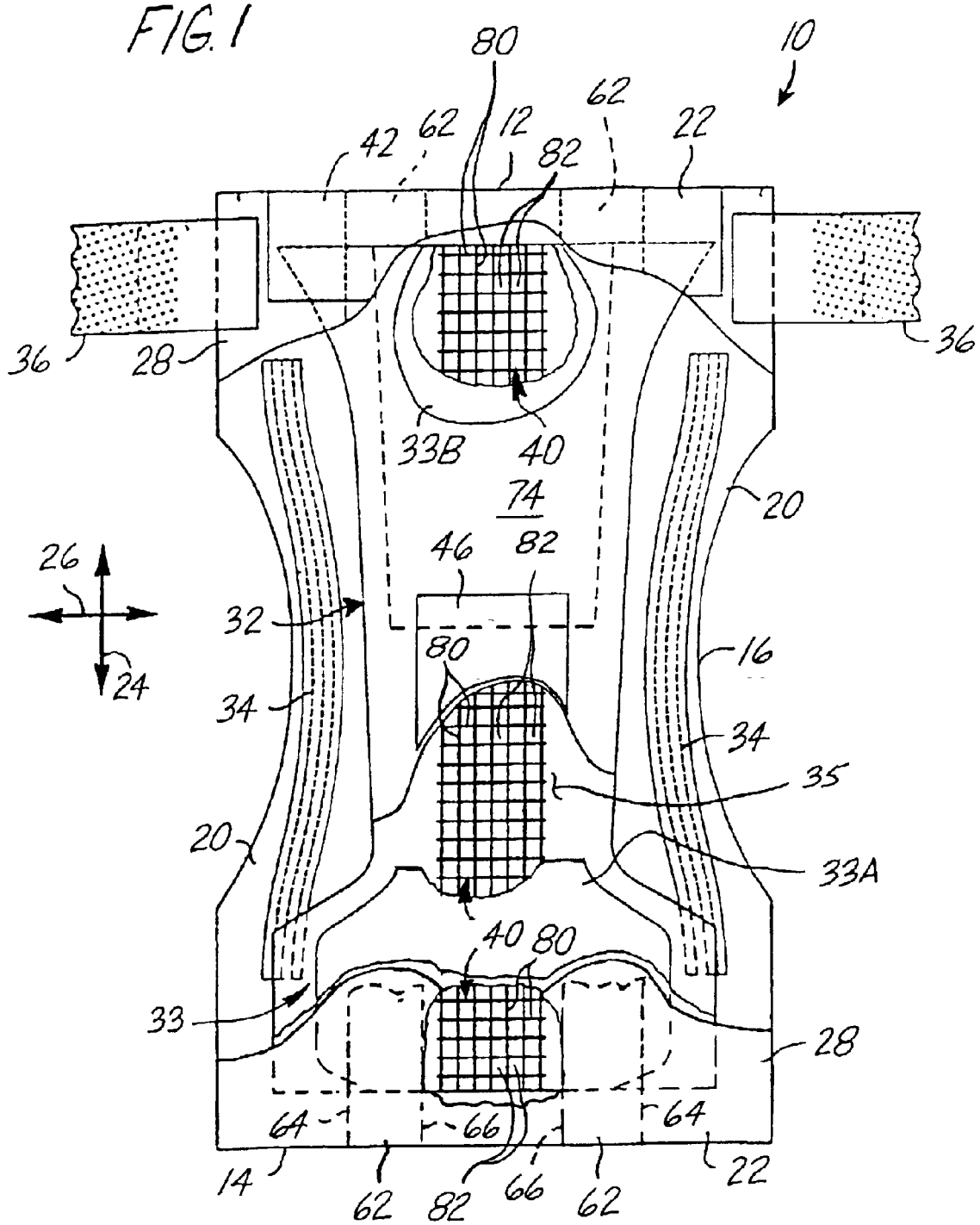
FIG. 1 is a partially cut-away, top plan view of an absorbent article in the form of a diaper.
Figure 2:
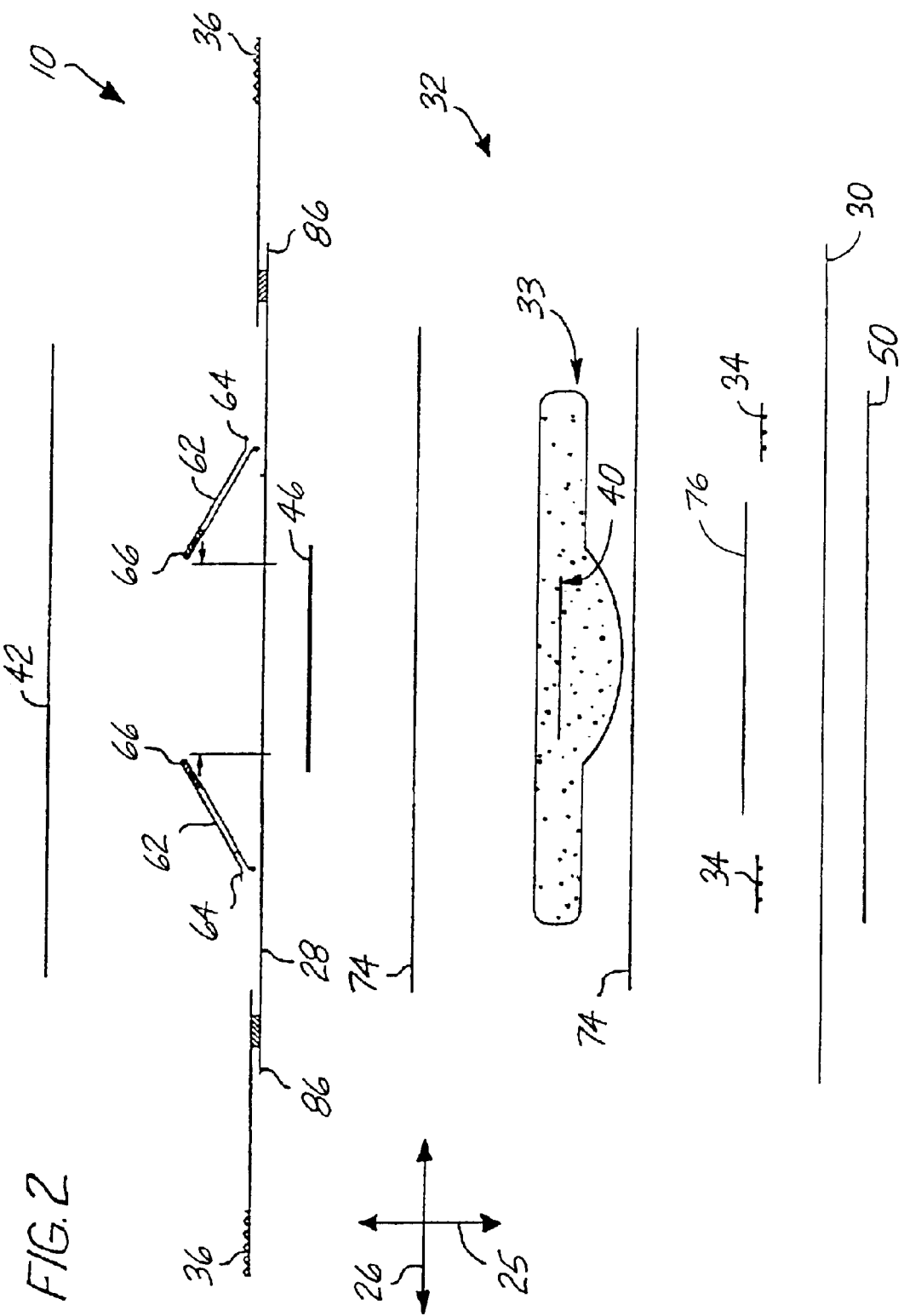
FIG. 2 is a schematic, exploded view, in section, of an absorbent article having an absorbent structure including a reinforcing member in the form of scrim.

Referring now to the drawings, and in particular to FIGS. 1 and 2, an absorbent article constructed according to the principles of the present invention is shown in the form of a diaper 10 unfolded and laid flat with substantially all elastic induced gathering and contraction removed. The diaper 10 extends lengthwise in a longitudinal or machine-direction 24, widthwise in a lateral or cross-direction 26, and has a thickness in a "z" or thickness direction 25. For the purposes of the present disclosure, the machine-direction 24 lies generally parallel to the plane of the diaper 10, and extends generally along a line that lies between an opposed pair of end regions of the diaper. The cross-direction 26 lies generally parallel to the plane of the article, and is aligned perpendicular to the longitudinal-direction 24. The z-direction 25 is aligned substantially perpendicular to both the machine-direction 24 and the cross-direction 26, and extends through the thickness of the diaper 10. In FIG. 1, the bodyside surface of the diaper which contacts the wearer is facing the viewer, and portions of the structure are partially cut away to more clearly show the interior construction of the diaper 10. The outer edges of the diaper define a periphery with longitudinally extending side edge margins 20 and laterally extending end edge margins 22. The side edges define leg openings for the diaper 10.

With regard to the designated surfaces of the article, the various inward or bodyside surfaces are arranged to face toward the body of the wearer when the article is placed about the wearer. The designated outward surfaces of the article are configured to face away from the wearer's body when the article is placed about the wearer. The diaper 10 may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The diaper 10 includes an absorbent structure, generally indicated at 32, having an absorbent core 33 (broadly, "an absorbent member") which can include absorbent fibers, nonabsorbent fibers and superabsorbent material (SAM). In the first embodiment illustrated in FIGS. 1–3, the absorbent core includes a front section 33A and a back section 33B unconnected to each other, except indirectly though their respective connections to other components of the diaper 10, and separated by a gap 35. A layer of scrim 40 (broadly, "a reinforcing member") is located generally in the middle of the absorbent core 33 for reinforcing the fibrous absorbent core to enhance the integrity of the core under loads as will be described more fully hereinafter. The scrim 40 extends between and interconnects the front and back sections 33A, 33B.

A backsheet layer 30 and a liquid permeable topsheet layer 28 are arranged opposite each other and the absorbent structure 32 is located between the backsheet layer and topsheet layer. Typically, the backsheet layer 30 is liquid impermeable, but may be liquid permeable without departing from the scope of the present invention. The illustrated diaper 10 has a first or back waistband portion 12, a second or front waistband portion 14 and an intermediate or crotch portion 16 that interconnects the back and front waistband portions. In use, the diaper 10 is fitted onto the lower torso and around the upper legs of a wearer (e.g., a child or infant), assuming a curved, three dimensional configuration in which parts of the back and front waistbands portions 12, 14 overlie or lie in close proximity to each other.

A fastening system includes fastener tabs 36 and a landing zone patch 50 (FIG. 2) for receiving the fastener tabs to interconnect the back waistband portion 12 with the front waistband portion 14 to hold the article on a wearer so that the back portion overlaps the front portion. However, a fastening system (not shown) could be used in which a front waistband portion overlaps the back waistband portion. In such optional arrangements, the front waistband portion would be the "first" waistband portion and the back waistband region would be the "second" waistband portion. It is to be understood that the present invention also has application to pre-fastened absorbent articles. The diaper also has a system of elastomeric gathering members, including leg elastics 34 to draw the diaper 10 around the legs and a waist elastic 42 (located in the back waistband portion 12) to draw the diaper around the waist.

The backsheet layer 30 is located along an outside surface of the absorbent structure 32 and may be composed of a liquid permeable material, but desirably comprises a material which is configured to be substantially impermeable to liquids. For example, a typical backsheet layer 30 can be manufactured from a thin plastic film, or other flexible, substantially liquid-impermeable material. As used in the present disclosure, the term "flexible" refers to materials which are compliant and which will readily conform to the general shape and contours of the wearer's body. The backsheet layer 30 can prevent the exudates contained in absorbent structure 32 from wetting articles, such as bedsheets and overgarments, which contact diaper 10. In particular embodiments of the invention, backsheet layer 30 can include a film, such as a polyethylene film, having a thickness of from about 0.012 millimeters (0.5 mil) to about 0.051 millimeters (2.0 mil). For example, the backsheet film can have a thickness of about 0.032 millimeters (1.25 mil).

Alternative constructions of the backsheet layer 30 may comprise a woven or non-woven fibrous web which has been totally or partially constructed or treated to impart the desired levels of liquid impermeability to selected regions that are adjacent or proximate the absorbent structure. For example, the backsheet layer 30 may include a gas-permeable, nonwoven fabric material laminated to an appointed facing surface of a polymer film material that may or may not be gas-permeable. Ordinarily, the fabric material is attached to an outward-facing surface of the polymer film material. Other examples of fibrous, cloth-like backsheet layer materials are a stretch-thinned or a stretch-thermal-laminate material composed of a 0.015 mm (0.6 mil) thick polypropylene blown film and a 23.8 g/m$^2$ (0.7 ounce per square yard) polypropylene spunbond material (2 denier fibers).

In particular arrangements, a substantially liquid impermeable, vapor permeable backsheet layer 30 may be a composite material which includes a vapor permeable film adhesively laminated to a spunbond material. The vapor permeable film can be obtained from Exxon Chemical Products Incorporated, under the tradename EXXAIRE. The film can include 48–60 weight percent (wt %) linear low density polyethylene and 38–50 wt % calcium carbonate particulates that may be uniformly dispersed and extruded into the film. The stretched film can have a thickness of about 0.018 mm (0.7 mil) and a basis weight of 16–22 grams per square meter (g/m$^2$). The spunbond material can be adhesively laminated to the film, and can have a basis weight of about 27 g/m$^2$. The spunbond material can be made using conventional spunbond technology, and can include filaments of polypropylene having a fiber denier of 1.5–3 dpf. The vapor-permeable film may be adhered to the spunbond material using a pressure sensitive, hot melt adhesive at an add-on rate of about 1.6 g/m$^2$, and the adhesive can be deposited in the form of a pattern of adhesive swirls or a random fine fiber spray. Another example of a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn.

The liquid impermeable, vapor permeable backsheet layer 30 may alternatively include a highly breathable stretch thermal laminate material (HBSTL). The HBSTL material can include a polypropylene spunbond material thermally attached to a stretched breathable film. For example, the HBSTL material may include a 20.4 g/m$^2$ (0.6 osy) polypropylene spunbond material thermally attached to an 18.7 g/m$^2$ stretched breathable film. The breathable film may include two skin layers with each skin layer composed of 1–3 wt % EVA/catalloy. The breathable film may also include 55–60 wt % calcium carbonate particulates, linear low density polyethylene, and up to 4.8% low density polyethylene. The stretched breathable film can include a thickness of 0.011–0.013 mm (0.45–0.50 mil) and a basis weight of 18.7 g/m$^2$. The spunbond material can be thermally bonded to the breathable film, and can have a basis weight of about 20.4 g/m$^2$. The spunbond material can have a fiber denier of 1.5–3 dpf, and the stretched breathable film can be thermally attached to the spunbond material using a "C-star" pattern that provides an overall bond area of 15–20%.

The various types of such materials have been employed to form the backsheet layer or outer cover of disposable diapers, such as HUGGIES disposable diapers which are commercially available from Kimberly-Clark Corporation. The article may include several components forming the backsheet layer. The backsheet layer 30 may also be embossed or otherwise provided with a pattern or matte finish to exhibit a more aesthetically pleasing appearance.

The topsheet layer 28 presents a body-facing surface that is compliant, soft-feeling, and non-irritating to the wearer's skin. Further, the topsheet layer 28 can be less hydrophilic than absorbent structure 32, and is sufficiently porous to be liquid permeable, permitting liquid to readily penetrate through its thickness to reach the absorbent structure. A suitable topsheet layer 28 may be manufactured from a wide selection of materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent structure 32. Various woven and nonwoven fabrics can be used for topsheet layer 28. For example, the topsheet layer may be composed of a meltblown or spunbonded web of the desired fibers, and may also be a bonded-carded-web. The various fabrics can be composed of natural fibers, synthetic fibers or combinations thereof. For the purposes of the present description, the term "nonwoven web" means a web of fibrous material that is formed without the aid of a textile weaving or knitting process. The term "fabrics" is used to refer to all of the woven, knitted and nonwoven fibrous webs.

The topsheet layer fabrics may be composed of a substantially hydrophobic material, and the hydrophobic material may optionally be treated with a surfactant or otherwise processed to impart a desired level of wettability and hydrophilicity. In a particular embodiment of the invention, topsheet layer 28 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% TRITON X-102 surfactant. Other types and amounts of operative surfactants may alternatively be employed. The surfactant can be applied by any conventional means, such as spraying, printing, brush coating or the like.

The topsheet layer 28 and backsheet layer 30 are connected or otherwise associated together in a suitable manner. As used herein, the term "associated" encompasses configurations in which topsheet layer 28 is directly joined to backsheet layer 30 by affixing topsheet layer directly to backsheet layer, and configurations wherein topsheet layer is indirectly joined to backsheet layer by affixing topsheet layer to intermediate members which in turn are affixed to backsheet. The topsheet layer 28 and backsheet layer 30 can, for example, be joined to each other in at least a portion of the diaper periphery in a suitable manner such as by adhesive bonding, some bonding, thermal bonding, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the topsheet layer 28 to the backsheet layer 30. It should be readily appreciated that the above-described attachment mechanisms may also be employed to suitably interconnect, assemble and/or affix together the various other component parts of the articles that are described herein.

The diaper 10 can also include a surge management member 46 which helps to decelerate and diffuse surges or gushes of liquid that may be rapidly introduced into the absorbent structure of the article. Desirably, the surge management member 46 can rapidly accept and temporarily hold the liquid prior to releasing the liquid into the absorbent structure 32. In the illustrated embodiment, for example, the surge member 46 can be located on an inwardly facing body side surface of the topsheet layer 28. Alternatively, the surge member 46 may be located adjacent to an outer side surface of the topsheet layer 28. Accordingly, the surge member 46 would then be interposed between the topsheet layer 28 and the absorbent structure 32. In one embodiment, the surge management layer comprises a nonwoven material having a basis weight of from about 20 to about 300 grams per square meter. Examples of suitable surge management members 46 are described in U.S. Pat. No. 5,486,166 entitled FIBROUS NONWOVEN WEB SURGE LAYER FOR PERSONAL CARE ABSORBENT ARTICLES AND THE LIKE by C. Ellis and D. Bishop, which issued Jan. 23, 1996; and U.S. Pat. No. 5,490,846 entitled IMPROVED SURGE MANAGEMENT FIBROUS NONWOVEN WEB FOR PERSONAL CARE ABSORBENT ARTICLES AND THE LIKE by C. Ellis and R. Everett, which issued Feb. 13, 1996; the entire disclosures of which are hereby incorporated by reference. However, it is to be understood that the surge management member 46 can be omitted without departing from the scope of the present invention. Where the absorbent core 33 is discontinuous, the surge management member 46 serves to transport any liquid in a region of the absorbent structure 32 which does not overlie the absorbent core to the absorbent core. In one embodiment, the length of the surge management member 46 is equal to or greater than the gap 35.

Elasticized containment flaps 62 extend generally lengthwise in the longitudinal direction 24 of the diaper 10. The containment flaps 62 are typically positioned laterally inboard from the leg elastics 34, and substantially symmetrically placed on each side of the lengthwise, longitudinal centerline of the diaper. In the illustrated arrangements, each containment flap 62 has a substantially fixed edge portion 64 and a substantially moveable edge portion 66, and is operably elasticized to help each containment flap to closely contact and conform to the contours of the wearer's body. Examples of suitable containment flap constructions are described in U.S. Pat. No. 4,704,116 entitled DIAPERS WITH ELASTICIZED SIDE POCKETS by K. Enloe which issued Nov. 3, 1987, the entire disclosure of which is hereby incorporated by reference. The containment flaps 62 may be composed of a wettable or a non-wettable material, as desired. In addition, the containment flap material may be substantially liquid-impermeable, may be permeable to only gas or may be permeable to both gas and liquid. The level of permeability of the containment flap material may be substantially the same as or different than the permeability of other components of the article. Other suitable containment flap configurations are described in U.S. Pat. No. 5,562,650 entitled ABSORBENT ARTICLE HAVING AN IMPROVED SURGE MANAGEMENT by R. Everett et al., which issued Feb. 13, 1996, the disclosure of which is hereby incorporated by reference.

In optional, alternative configurations of the invention, diaper 10 may include internal, elasticized, containment waist flaps, such as those described in U.S. Pat. No. 4,753,646 entitled DIAPER WITH WAIST FLAPS by K. Enloe which issued Jun. 28, 1988; and in U.S. Pat. No. 5,904,675 entitled AN ABSORBENT ARTICLE WITH IMPROVED ELASTIC MARGINS AND CONTAINMENT SYSTEM by D. Laux et al., which issued May 18, 1999; the entire disclosures of which are hereby incorporated by reference. Similar to the construction of the containment flaps 62, the containment waist flaps may be composed of a wettable or non-wettable material, as desired. The waist flap material may be substantially liquid-impermeable, permeable to only gas, or permeable to both gas and liquid.

The landing zone patch 50 provides a target area for releasable and re-attachable securement with the fastener tabs 36. The landing zone patch 50 is positioned on the front waistband portion 14 of the diaper 10 and located on the outward surface of the backsheet 30 in the illustrated embodiment. Alternatively, the landing zone patch 50 could be positioned on an inward surface of the diaper 10, such as the bodyside surface of the topsheet layer 28, or at any other suitable location. Particular arrangements of the invention can include one or more landing zone patches that can be directly or indirectly attached to the second waistband portion 14. The landing zone patch 50 can be composed of a substantially non-elastomeric material, such as polymer films or tapes, woven fabrics, nonwoven fabrics or the like, as well as combinations thereof. The landing zone patch 50 could also be made of a substantially elastomeric material, such as a stretch-bonded-laminate (SBL) material, an elastomeric neck-bonded-laminate (NBL) material, an elastomeric film, an elastomeric foam material, or the like, which is elastomerically stretchable at least along the lateral direction 26.

The fastener tabs 36 are located at rearward portions of the side edges 20 near the back waistband portion 12, but could be located at front portions of the side edges near the front waistband portion 14. The fastener tab 36 can be made of a substantially non-elastomeric material, such as polymer films or tapes, woven fabrics, nonwoven fabrics or the like, as well as combinations thereof. Optionally, the fastener tabs 36 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 26.

In the various aspects and configurations of the invention, the fastening mechanism between the selected first fastener component and the selected, second fastener component may be adhesive, cohesive, mechanical or combinations thereof. In the context of the present invention, a mechanical fastening system is a system that includes cooperating, first and second components that mechanically inter-engage to provide a desired securement. Desirably, the first and second fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components.

As shown in the illustrated embodiment, the mechanical fastening system is of the hook-and-loop type. Such fastening systems typically include attachment members having the form of a "hook" or hook-like, male component, and include a cooperating "loop" or loop-like, female component that engages and releasably interconnects with the hook component. Desirably, the interconnection is selectively releasable and re-attachable. Conventional systems are, for example, available under the VELCRO trademark. The hook element may be provided by a single-prong hook configuration, a multiple-prong hook configuration or by a generally continuous, expanded-head configuration, such as provided by a mushroom-head type of hook element. The loop element may be provided by a woven fabric, a non-woven fabric, a knitted fabric, a perforated or apertured layer, and the like, as well as combinations thereof. The many arrangements and variations of such fastener systems have been collectively referred to as hook-and-loop fasteners. As illustrated, the hook element is located on the fastener tab 36 and the loop element defines the patch 50, but the arrangement of the hook element and the loop element could be reversed.

The absorbent structure 32 has a construction that is generally compressible, conformable, non-irritating to the wearer's skin, and capable of absorbing and retaining body exudates. It should be understood that, for purposes of this invention, the absorbent structure 32 comprises several parts that are assembled together. The absorbent core 33 of the absorbent structure 32 may be constructed of any of a number of absorbent materials, as are well known in the art. For example, the absorbent core 33 may be provided by a layer of coform, meltblown fibers, bonded carded webs, a wetlaid body, tissue laminates, foams, a surge/air formed composite and the like or combinations thereof. In particular, the absorbent core 33 may be provided as a combination of hydrophilic fibers, and high-absorbency material.

In the illustrated embodiment, the absorbent core 33 is zoned, having a selected zone of higher basis weight. There may be multiple zones or portions of the absorbent core selected to have particular properties. In the illustrated embodiment the zone is constructed and arranged to provide for additional retention of liquid (as compared to the other regions of the core 33). The zone may be positioned in a location where maximum absorbent capacity is needed. A description of one way to form zoned absorbent cores are disclosed in co-assigned U.S. Pat. No. 4,761,258 entitled CONTROLLED FORMATION OF LIGHT AND HEAVY FLUFF ZONES by K. Enloe which issued Aug. 2, 1988; U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001; and U.S. patent application Ser. No. 10/207,929, filed Jul. 30, 2002 (attorney docket No. 16,900), entitled APPARATUS AND FORM FOR MAKING AN AIR FORMED FIBROUS WEB by Venturino et al., the disclosures of which are incorporated by reference.

Various types of wettable, hydrophilic fibrous material can be used to provide the fiber material for the absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material that has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

The high-absorbency material used in the absorbent structure 32 may comprise absorbent gelling materials, such as superabsorbent materials. Absorbent gelling materials can be natural, biodegradable, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces. Examples of synthetic absorbent gelling material polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbent materials are well known in the art, and are readily available from various suppliers. For example, FAVOR SXM 880 superabsorbent is available from Stockhausen, Inc., a business having offices located in Greensboro, N.C., U.S.A.; and DRYTECH 2035 is available from Dow Chemical Company, a business having offices located in Midland, Mich., U.S.A.

The high-absorbency material used in the absorbent core 33 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in the absorbent core 33. Desired for use are particles having an average size of from about 20 micrometers to about 1 millimeter. "Particle size" as used herein means the weighted average of the smallest dimension of the individual particles.

The absorbent materials and superabsorbent materials may be integrated into the absorbent web by employing any operative method or apparatus. For example, the absorbent web may be formed with a dry-forming technique, an air forming technique, a wet-forming technique, a foam-forming technique or the like, as well as combinations thereof. Certain methods and apparatus for carrying out such techniques are well known in the art.

Referring again to FIGS. 1 and 3, the absorbent core 33 of the first embodiment is shown to have a zone having a higher air permeability than an adjacent lower air permeability zone(s) of the absorbent core 33. The front core section 33A is spaced in the longitudinal direction 24 from the back section 33B to define the gap 35 between the front and back sections. In use of the diaper 10, the gap 35 defines a higher air permeability zone or passage for air (and vapor) through the absorbent structure 32 to the wearer's skin for ventilating the skin.

Generally speaking the higher air permeability zones (e.g., passages or gap) of the present invention constitute at least about 5% of the total area of one major surface of the absorbent core 33. More particularly, the higher air permeability zones constitute between about 5% and 75% of the total area of at least one major surface of the core 33. The ventilation provided by the higher air permeability zones preferably allows the diaper 10 to have a skin hydration value of less than about 18 grams per square meter per hour. More preferably, the skin hydration value is less than about 15 grams per square meter per hour. However, it is to be understood that the characteristics of the diaper may fall outside these specific ranges without departing from the scope of the present invention.

Skin hydration values are determined by measuring total evaporative water loss (EL) and can be determined by employing the following test procedure. The test is conducted on partially toilet trained infants who have no lotions or ointments on the skin and have not been bathed within 2 hours prior to the test. Each infant tests one diaper during each test session. Each test diaper is weighed before and after use to verify the volume of liquid added into the diaper. A felt tip pen is employed to mark an "X" at the target zone inside the diaper, with the "X" positioned 6.5 inches below the top front edge of the diaper and centered side-to-side. The EL measurements are taken with an evaporimeter, such as an Evaporimeter EP1 instrument distributed by Servomed AB, Stockholm, Sweden. Each test measurement is taken over a period of two minutes with EWL values taken once per second (a total of 120 EWL values). The digital output from the Evaporimeter EP1 instrument gives the rate of evaporative water loss (EWL) in $g/m^2/hr$. Skin hydration values (SHV) are in units of total amount of water loss per unit area measured during the two-minute sampling period and are calculated as follows.

$$SHV(g/m^2/hour) = \frac{\sum_{n=1}^{120}(EWL)_n}{120}$$

A preliminary skin hydration value measurement is taken after a 15-minute "dryout" period when the infant wears only a long T-shirt or dress and is in the supine position. The measurement is taken on the infant's lower abdomen, in a region corresponding to the target zone of the diaper, using the evaporimeter for the purpose of establishing the initial skin hydration value of the infant's skin at the diaper target zone. If the preliminary SHV is less than 10 $g/m^2$/hour, a diaper is then placed on the infant. If the preliminary SHV is greater than 10 $g/m^2$/hour, the "dryout" period is extended until a reading below 10 $g/m^2$/hour is obtained. Prior to securing the diaper on the infant, a tube is positioned to direct a flow of liquid to hit the premarked target zone. Once the diaper is secured, 210 milliliters of adjusted 0.9 weight percent aqueous saline is added in three insults of 70 milliliters each at a rate of 15 ml/s with a 45 second delay between insults.

The infant wears the diaper for 60 minutes after which the diaper is removed and a test measurement of skin hydration is taken on the lower abdomen corresponding to the target zone mark of the diaper. The measurement is taken over a 2-minute period. The used diaper is then weighed. Relative humidity and temperature measurements can be taken within the diaper prior to the skin hydration measurements being taken.

Data is discarded for any infants who have added to the loading of saline solution. The value reported for the mean net SHV ($g/m^2$/hour) is the arithmetic mean for all infants of the post-wear skin hydration value, taken at the lower abdomen (target zone mark), minus the skin hydration value measured at the lower abdomen prior to placing the diaper on the infant (after "dryout" period).

The net skin hydration value is determined as follows:

Net $SHV_I = Y - Z$

Where:
- Y=skin hydration value measured at target zone mark of an individual infant
- Z=baseline skin hydration value measured on the lower abdomen after "dryout" period prior to placing diaper on the infant
- $SHV_I$=skin hydration value for individual infant Then, $$\text{Mean Net } SHV = \frac{\sum_{i=1}^{N} \text{Net } SHV_i}{N}$$

Where:

N=number of infants in study

Figure 3:
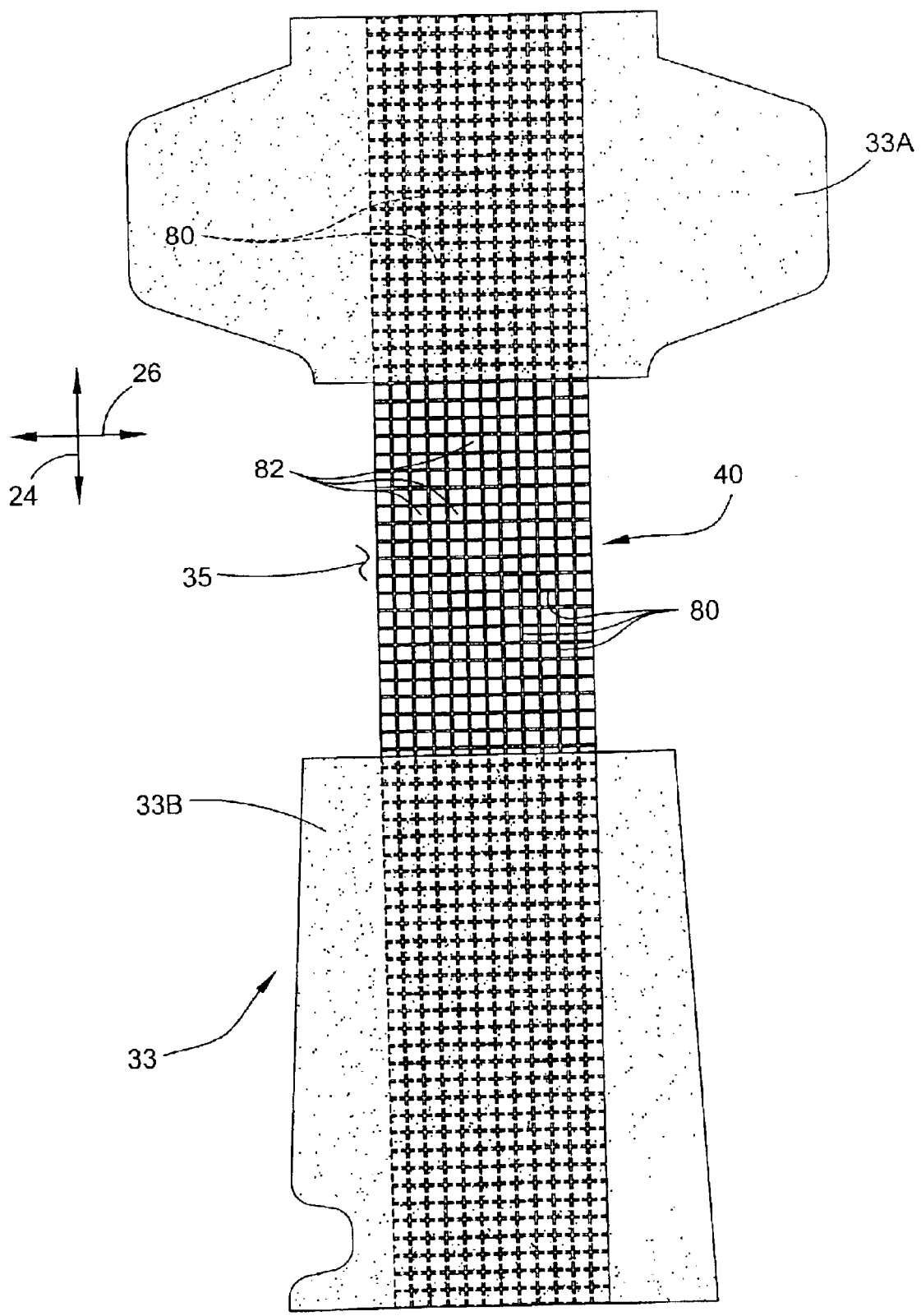
FIG. 3 is a top plan view of an absorbent core of the absorbent structure of the diaper of FIG. 1.

As may be seen in FIG. 3, the front and back sections 33A, 33B of the absorbent core 33 are distinct and have no absorbent material in contact with each other. Thus, there is no structural interconnection between the sections 33A, 33B of the absorbent core 33 provided by the fibrous material forming a majority of the core. The core 33 itself provides no structure to locate the front and back sections 33A, 33B relative to each other. Examples of discontinuous absorbent cores are given in co-assigned U.S. Pat. No. 6,296,862, entitled ABSORBENT ARTICLE WHICH MAINTIAINS OR IMPORVES SKIN HEALTH, by Paul et al., which issued Oct. 2, 2001, the disclosure of which is incorporated herein by reference. It is to be understood that an absorbent core of the present invention may include more than two sections (not shown).

End portions of the scrim 40 are embedded in each of the core sections 33A, 33B, and the scrim bridges the gap 35 between the core sections. The scrim 40 comprises elongate strands 80 which are arranged so that the strands intersect each other at junctions. More specifically, the strands 80 are arranged in a grid including parallel strands extending in the longitudinal direction 24 and strands extending in the lateral direction 26 defining rectangular openings 82 in the scrim. Among other things, the openings 82 permit liquid in the absorbent core sections 33A, 33B to flow substantially unhindered through the scrim 40. The strands 80 are secured to each other where they intersect to create a lattice providing strength such as but not limited to tensile, compressive, and shear. The scrim 40 also has sufficient rigidity to assist in holding the front core section 33A in a substantially fixed position relative to the back section 33B within the diaper 10. Moreover, the scrim 40 reinforces each of the sections 33A, 33B internally against clumping, sagging, tearing, etc. Thus, the sections 33A, 33B will retain their desired configurations and relative positions when subjected to forces applied by movement of the wearer and under loads from urine insults.

The scrim 40 provides advantages during manufacture of the diaper 10 (or other absorbent article). In one embodiment, the absorbent core sections 33A, 33B are air formed on a drum. Although the sections 33A, 33B are discontinuous and separated, the scrim 40 extends continuously from one section to the other and from one absorbent core 33 to the other. Thus, force needed to dislodge the absorbent core sections 33A, 33B from the drum is borne not only by the material of each core section 33A, 33B, but also by the scrim 40 to continuously peel the sections off of the drum. It is unnecessary to independently capture each section 33A, 33B from the drum because of their scrim interconnection. Moreover, the scrim reinforces the absorbent core sections 33A, 33B so that they are less likely to tear under the forces experienced when being peeled from the drum. The scrim 40 also makes it easier to retain control of the core sections 33A, 33B downstream in the manufacturing process. The sections 33A, 33B are structurally unitized by the interconnecting scrim 40 so that they are more like a large single piece absorbent core, which is easier to control in automated machinery used in the assembly of the diaper 10.

Figure 4A:
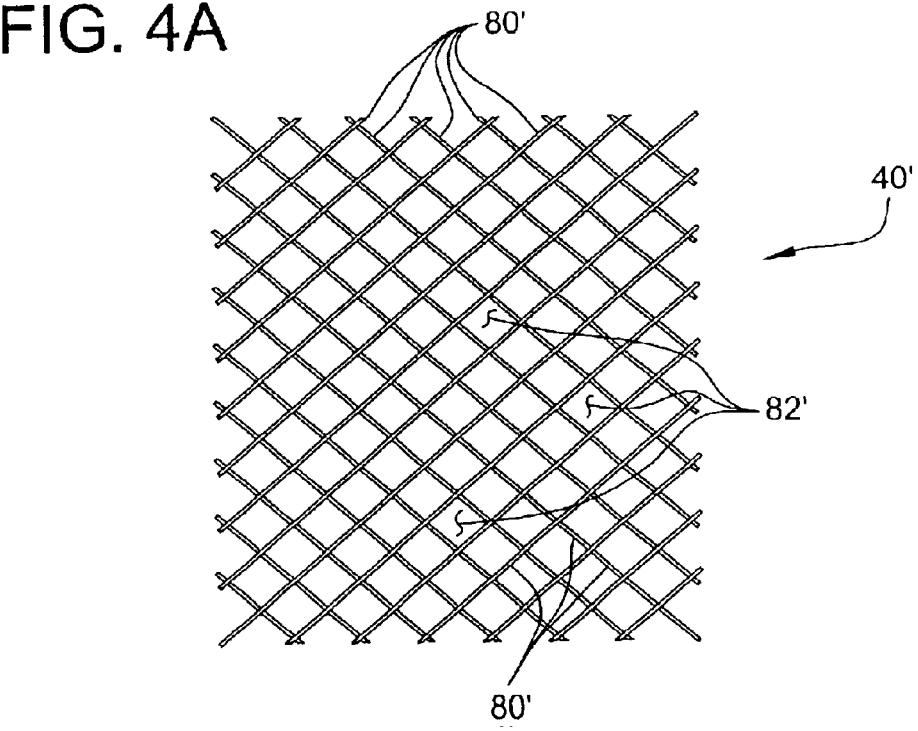
FIG. 4A is a plan view of a reinforcing member in the form of scrim material having diamond shaped openings.
Figure 4B:
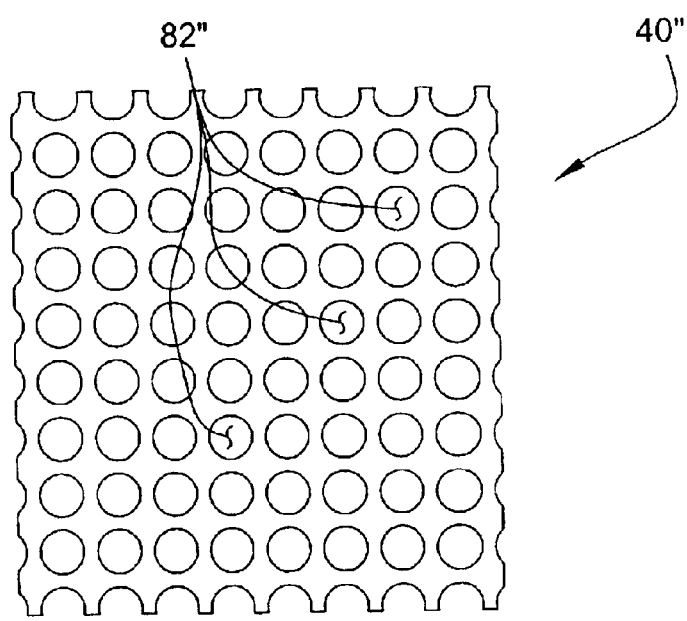
FIG. 4B is a plan view of a reinforcing member in the form of apertured sheet material.

The scrim 40 can be made of any suitable material that provides desired levels of strength and flexibility. For example, the strands 80 of the scrim 40 may be composed of natural or synthetic materials, as well as combinations thereof. In a particular arrangement, the material of the strands 80 may include a synthetic polymer (e.g., polyester, polyethylene, polypropylene, rayon). The synthetic polymer may be monofilament or bicomponent. Natural materials that could be used include cotton, jute, hemp, wool. Alternate materials include glass, carbon and metallic fibers. The reinforcing scrim 40 can be a woven or nonwoven material. The scrim strands in the machine-direction 24 and cross-direction 26 could be of different materials. Alternately different materials could be used in alternating scrim strands in the machine-direction 24 and/or cross-direction 26. In one embodiment, the strands 80 may be formed of or coated with a superabsorbent material. In that event, the scrim 40 would serve a liquid retention function in addition to its reinforcing function. An example of a superabsorbent coating is given in co-assigned application Ser. No. 10/246,811 entitled ABSORBENT ARTICLES HAVING A SUPERABSORBENT RETENTION WEB by Newbill et al., filed Sep. 18, 2002 (attorney docket No. 16,739), the disclosure of which is incorporated herein by reference. The strands may be arranged so as to form rectangular, square, diamond-shaped, curved or otherwise shaped openings without departing from the scope of the present invention. An example of scrim 40' having strands 80' arranged to form diamond-shaped openings 82' is shown in FIG. 4A. The "reinforcing member" may be other than scrim, such as a perforated, elastic film or individual strands or webs of material extending through the absorbent core. A reinforcing member 40" is shown in FIG. 4B in the form of a film having openings 82" formed by perforations in the film. A suitable scrim material is RO03230 Polypropylene Scrim material available from Conwed Plastics, a business having offices in Minneapolis, Minn., U.S.A.

The scrim 40 may be incorporated in the absorbent core 33 in a suitable manner, such as during the formation of the absorbent core. Suitable air forming methods and apparatus for such incorporation are disclosed in co-assigned U.S. patent applications Ser. No. 10/306,269, entitled PROCESS AND APPARATUS FOR MAKING A REINFORCED FIBROUS ABSORBENT MEMBER, by Venturino et al., (attorney docket no. 16,836A), Ser. No. 10/305,755, entitled PROCESS AND APPARATUS FOR AIR FORMING AN ARTICLE HAVING A PLURALITY OF REINFORCED SUPERIMPOSED FIBROUS LAYERS, by Heyn et al. (attorney docket no. 17,821.1), and Ser. No. 10/306,186, entitled CONTROLLED PLACEMENT OF A REINFORCING WEB WITHIN A FIBROUS ABSORBENT, by Venturino et al., (attorney docket no. 18,613), all filed simultaneously herewith. The disclosures of these applications are incorporated herein by reference. It is noted that these forming methods and apparatus promote the entanglement of the fibers in the absorbent core 33 with the scrim 40 (e.g., as by wrapping of the fibers around the strands 80 of the scrim during the air forming process) and with each other during manufacture of the absorbent core.

This type of interconnection is described in co-assigned U.S. patent application Ser. No. 10/306,086, entitled ABSORBENT ARTICLE WITH REINFORCED ABSORBENT STRUCTURE, by Heyn et al., filed simultaneously with the present application (attorney docket no. 16,836B). The disclosure of this application is incorporated by reference. A specific forming apparatus and method particularly suited for the absorbent structure 32 of the present invention are described hereinafter. The reinforcing member may take forms other than scrim 40 which are capable of holding the relative positions of the core sections 33A, 33B. for instance, some of the forms of the reinforcing member described in co-assigned application Ser. No. 10/306,086 (attorney docket no. 16,836B) could be used.

Figure 5A:
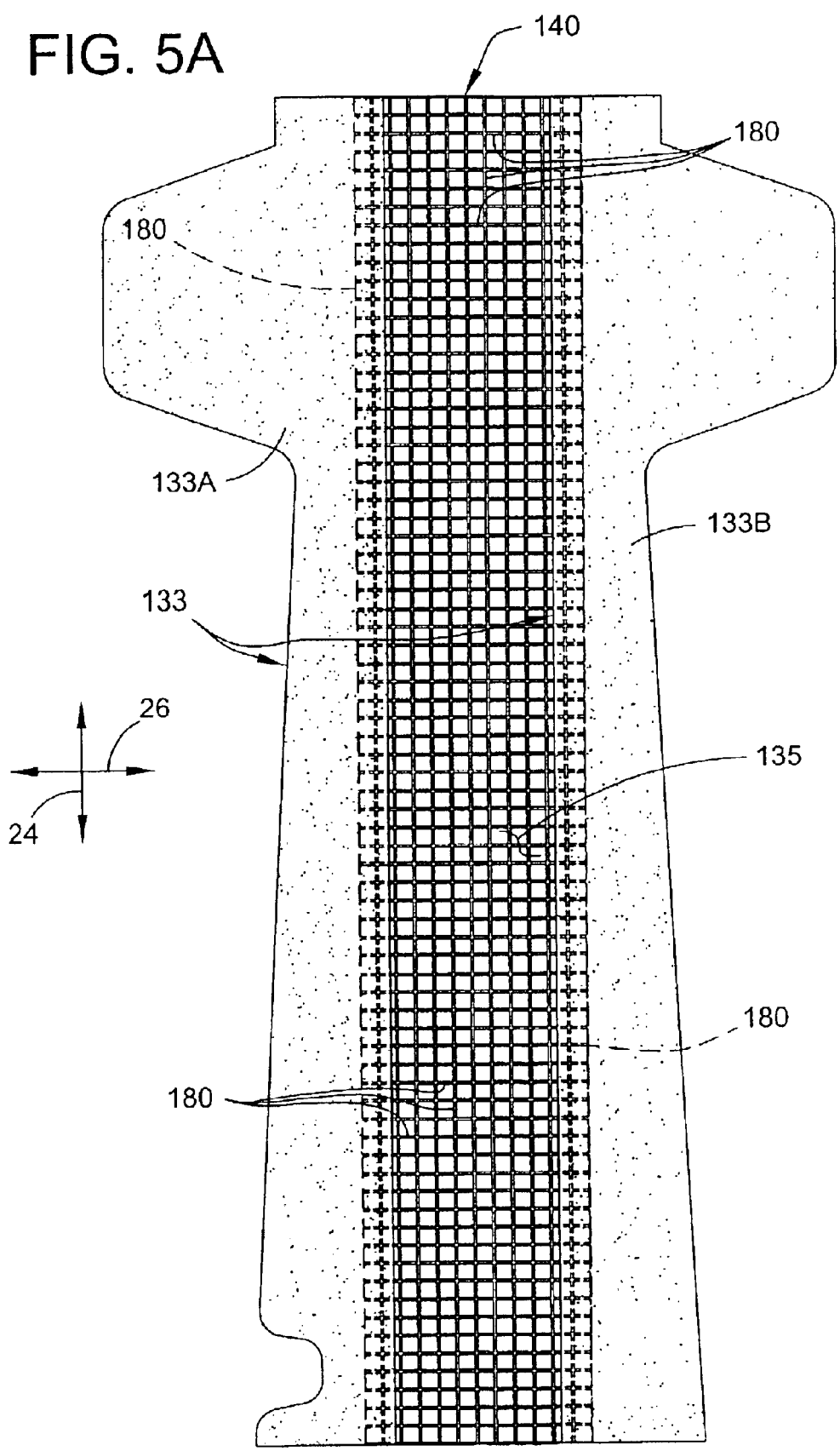
FIG. 5A is a top plan view of an absorbent core of a second embodiment which is discontinuous in a lateral direction of the absorbent structure.

Referring now to FIG. 5A, an absorbent core 133 of a second embodiment of the present invention is shown to comprise a left core section 133A and a right core section 133B separated by a gap 135. As with the first embodiment, no portion of the absorbent fibers of one core section 133A contacts the other core section 133B. The core sections 133A, 133B are connected together by a reinforcing member in the form of scrim 140. Longitudinal edge margins of the scrim 140 are embedded in respective core sections 133A, 133B. The strands 180 extending in the cross-direction 26 connect the two scrim sections 133A, 133B together. The scrim 140 has the same construction illustrated in FIGS. 1–3, and could also have the same alternative constructions which provide lateral connection between the scrim sections 133A, 133B. The gap 135 between the core sections 133A, 133B is narrowed when a diaper (or other absorbent article, not shown) is donned. The absorbent core 133 is laterally compressed between the wearer's legs in the crotch so that the gap 135 is narrowed or closed at the crotch. The lateral constriction of the absorbent core 133 places the left and right absorbent sections 133A, 133B in a more central position to absorb urine and other exudates. In addition, other liquid permeable components of the diaper overlying (or underlying) the gap 135 can also function to transfer liquid to the absorbent core sections 133A, 133B.

Figure 5B:
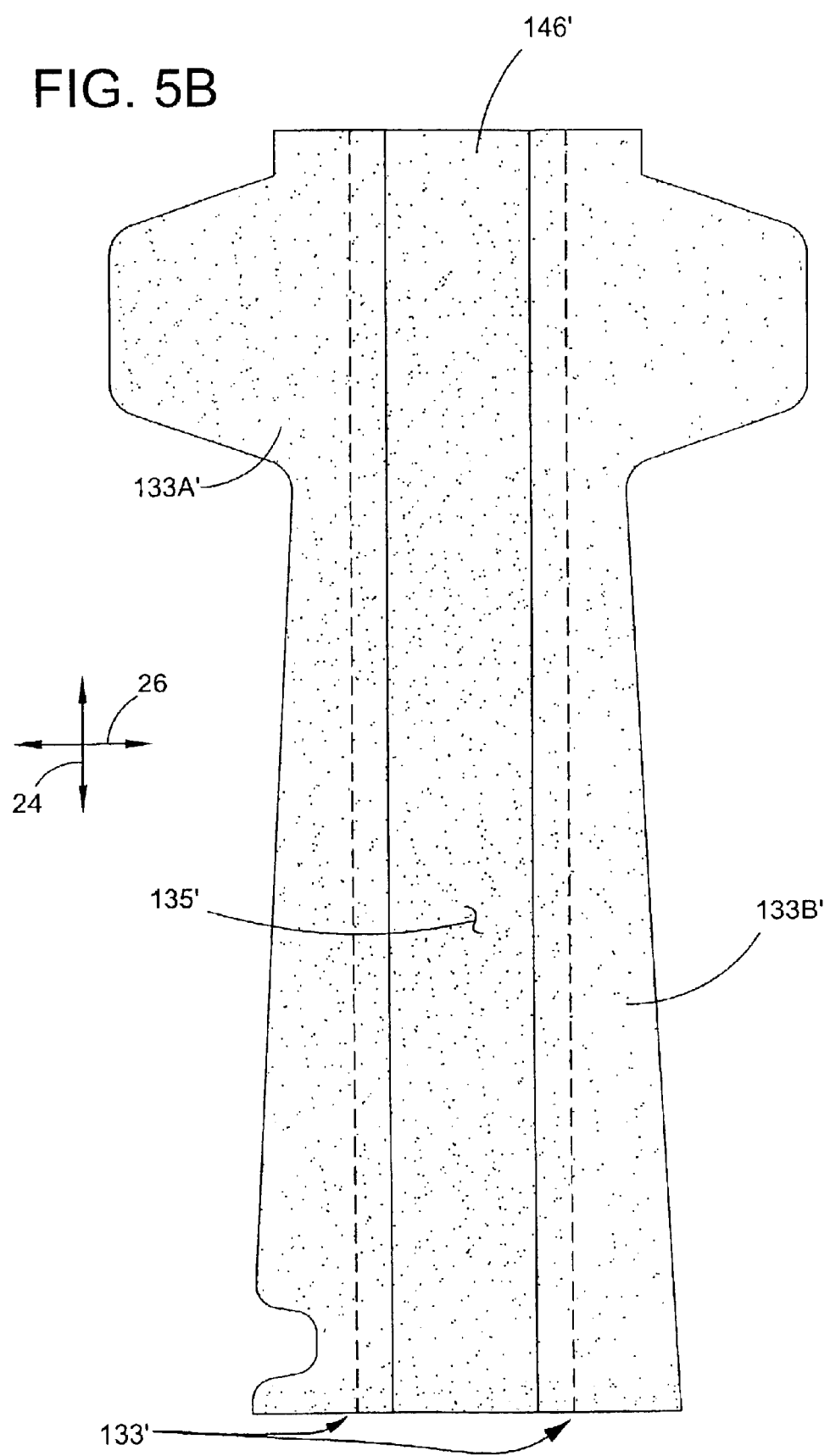
FIG. 5B is a top plan view of an absorbent core similar to FIG. 5A, but having a different reinforcing member.

Referring to FIG. 5B, it is also envisioned that instead of the scrim 140, other air and liquid permeable material (broadly, "a lofty nonwoven material") such as a surge member 146' could be used as the reinforcing member to structurally connect left and right core sections 133A', 133B' together across a gap 135'. The air permeability of the surge member 146' allows it to achieve ventilation of the skin through the absorbent core 133', and the liquid permeability facilitates transport of liquids to the absorbent core sections 133A', 133B'. The surge member 146' may be joined to the core sections 133A', 133B' in any suitable manner such as by bonding or fiber entanglement or some combination of connection mechanisms. The dashed lines of FIG. 5B represent the edges of the surge member 146' within the core sections 133A', 133B'. It is also envisioned that a surge member (not shown, but similar to surge member 146') could be used in place of scrim 40 in the absorbent core configuration shown in FIG. 3.

Figure 6A:
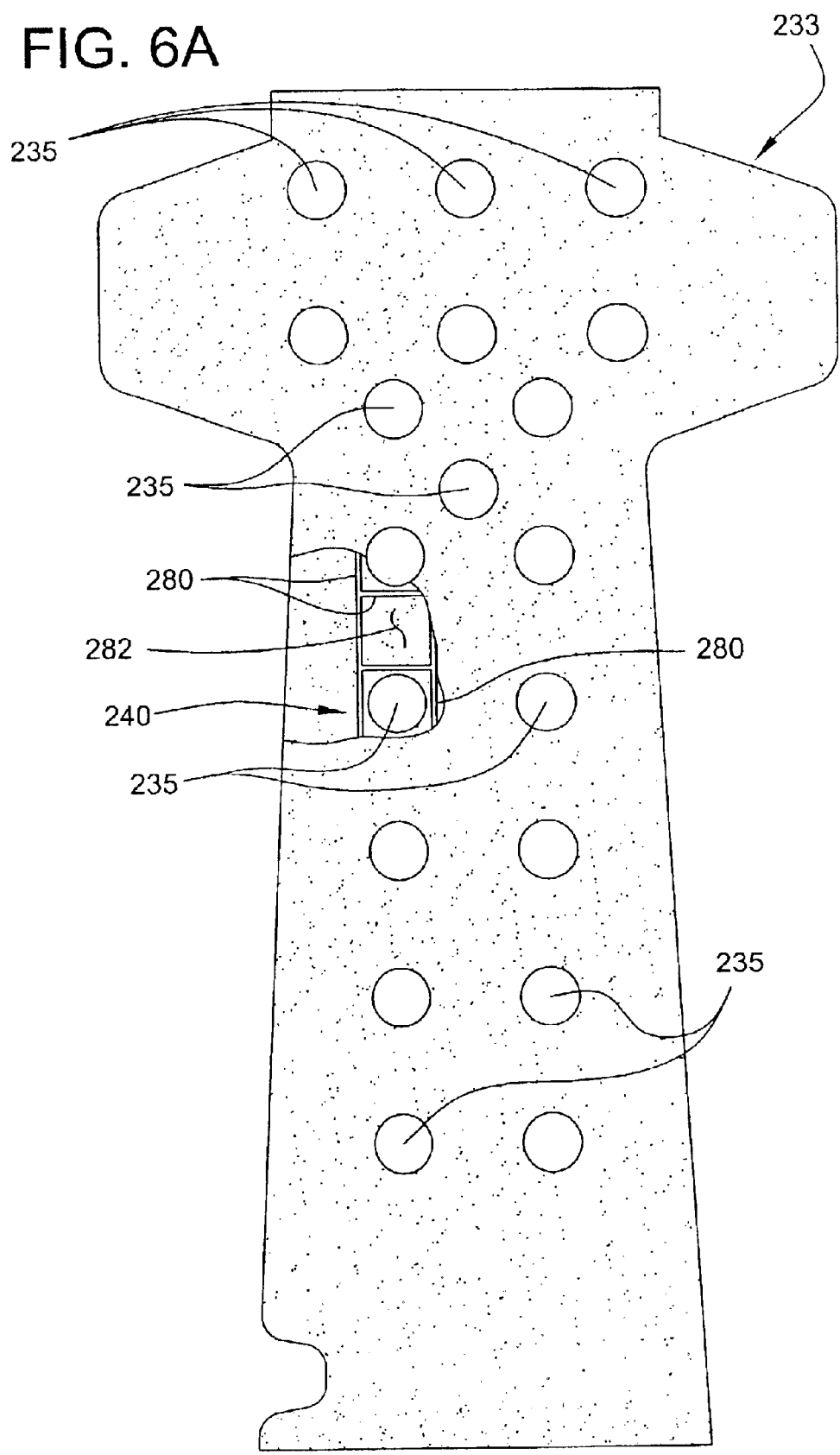
FIG. 6A is a top plan view of an absorbent core of a third embodiment having multiple openings therein, and with parts broken away to illustrate a reinforcing member.

A third embodiment of the absorbent core 233 is shown in FIG. 6A to include a multiplicity of openings 235 through the absorbent core. In this embodiment, the openings 235 define a zone of higher air permeability or passage for passing air (and vapor) through the absorbent core 233. In the first two embodiments, the discontinuity was provided by a complete separation of absorbent material in the absorbent core (33, 133). However unlike the first two embodiments, there are no core sections which are completely unconnected by absorbent material. The openings 235 constitute the discontinuity in the absorbent core 233 of the third embodiment. Although plural openings 235 in the absorbent core 233 are shown, a single opening or gap may be used without departing from the scope of the present invention. Such a single opening may be entirely surrounded by absorbent material (not shown) or a separating gap 35, 135, 135' as shown in FIGS. 3, 5A and 5B. The scrim 240 is embedded within the core 233 and extends substantially the full length of the core. However, the scrim may extend less than the full length. The scrim 240 is sized so that its longitudinal edges are spaced inward from the longitudinal edges of the absorbent core 233 so that the edges of the scrim are not exposed. The scrim 240 is located about midway through the thickness of the core 233 if the core is flat (i.e., has a substantially constant thickness), but could be located elsewhere within the thickness of the core without departing from the scope of the present invention. Where the absorbent core has differing thicknesses, the location of the scrim with respect to either major surface of the core will vary over the core.

The scrim 240 has openings 282 which are aligned with the openings 235 in the absorbent core 233. Thus, the scrim 240 provides no obstruction to air flow through the core opening 235. Moreover, the scrim 240 has maximum interconnection with the fibers of the core 233. The more of the length of strands 280 which is embedded within the core, the more entanglement with the fibers of the core with the strands there will be. Fiber entanglement with the scrim 240, and entanglement of fibers with each other through the scrim connects the core 233 and scrim together.

Figure 6B:
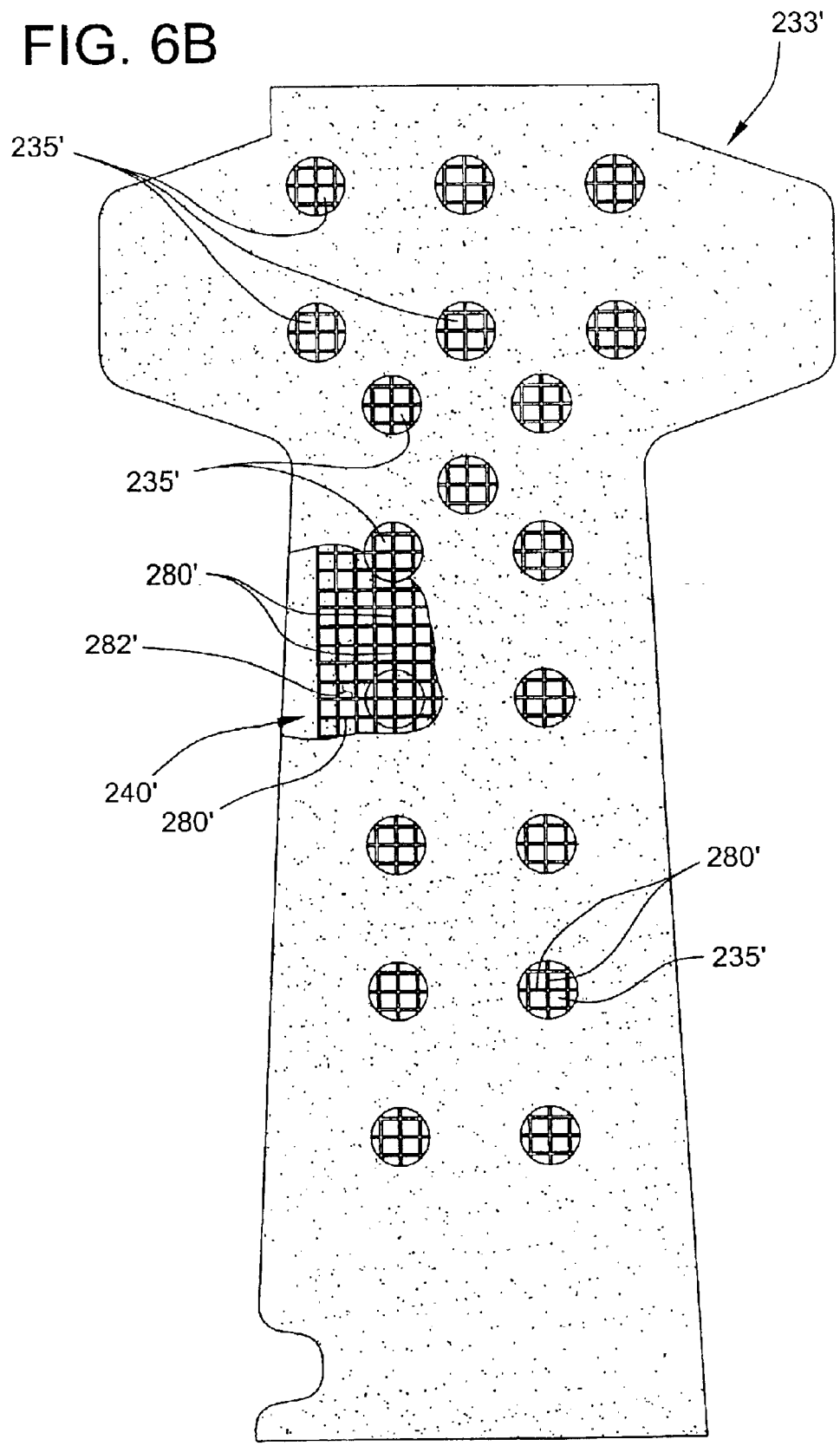
FIG. 6B is a top plan view similar to FIG. 6A, but showing a modified absorbent core.

In a modified third embodiment shown in FIG. 6B, the scrim 240' is sized and arranged relative to the size and position of the openings 235' in the absorbent core 233' so that junctions of lateral and longitudinal strands 280' are located within the openings. The junctions of the strands 280' may be centered on the openings 235' (as shown) or otherwise positioned within the openings. For scrim having smaller mesh sizes (not shown), multiple junctions may appear in a single opening of the absorbent core. It is believed this arrangement provides resistance to collapse of the opening 235', particularly when the absorbent core 233' becomes loaded with liquid. In this way, the scrim 240' helps to maintain breathability of the absorbent core 233'. The presence of more scrim strands 280' in the opening 235' is also believed to resist tears of the absorbent core 233' at the openings. The scrim in the openings 235' never-the-less provides minimal obstruction to ventilating air flow through the openings.

Figure 6C:
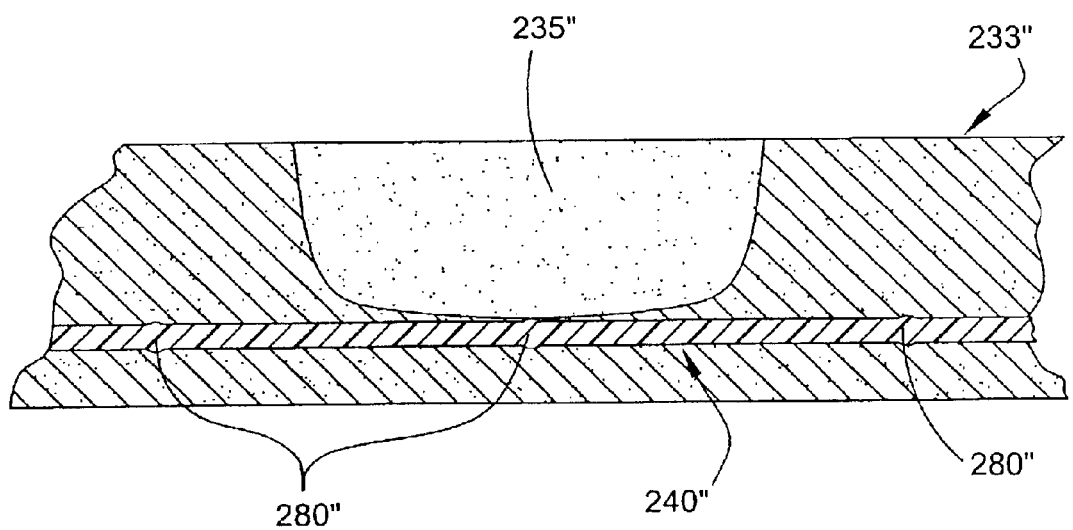
FIG. 6C is a fragmentary cross section of an absorbent core of another modified third embodiment having dimples in place of multiple openings.

Referring to FIG. 6C, a further modified third embodiment of the absorbent core 233" has dimples 235" rather than openings (e.g., openings 235, 235'). FIG. 6C illustrates only a fragmentary cross section of the further modified absorbent core 233" taken through one of the dimples 235". The absorbent core 233" has a similar construction to the core 233' of FIG. 6B except that the dimples 235" extend only part way through the thickness of the core. The appearance of the surface of the absorbent core 233" having the dimples 235" in it would be similar to FIG. 6B. The dimples 235" may be circular or otherwise shaped, and are areas of reduced thickness and/or basis weight of the absorbent material making up the absorbent core 233". The reduced basis weight allows each dimple 235" to more readily pass ventilating air (and vapor) to and from the wearer's skin through the absorbent core 233", whereby the dimples 235" form zones of higher air permeability through the absorbent core. The scrim 240" reinforces the absorbent core 233" in the same way as the scrim 240, 240'.

Figure 6D:
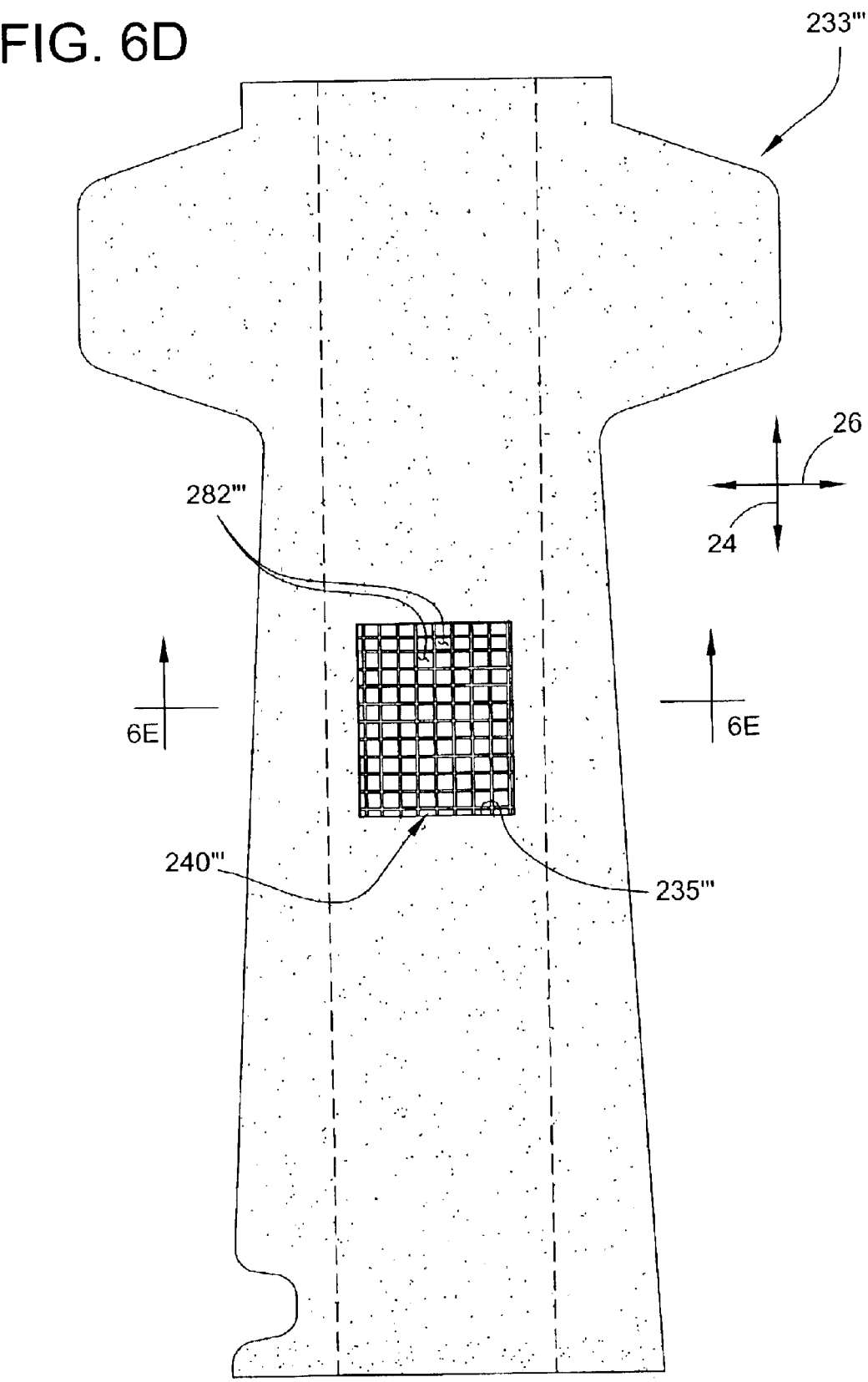
FIG. 6D is a top plan view similar to FIG. 6A, but showing an absorbent core of a fourth modified version.
Figure 6E:
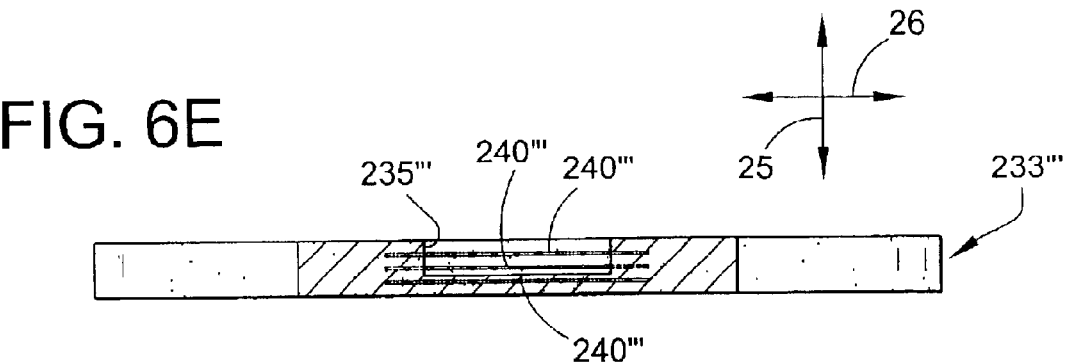
FIG. 6E is a section taken in the plane including line 6E—6E of FIG. 6D.

A still further modified absorbent core 233''' is shown in FIGS. 6D and 6E to have a single, relatively large opening or "void" 235''' therein. It will be understood that the number of openings may be greater than one, as described previously. The void 235''' extends only part way through the thickness of the absorbent core 233''' so that it forms a pocket in the absorbent core. Although shown as rectangular, the void 235''' could have other shapes without departing from the scope of the present invention. The void 235''' may define a liquid collection volume for collecting a surge of liquid during urination for subsequent absorption into the absorbent core 233''', or it may serve as a trap for a bowel movement. The strength and integrity of the absorbent core 233''' is maintain by scrim 240''' embedded in the material of the absorbent core. The presence of the scrim 240''' allows a significantly large amount of material of the absorbent core 233''', corresponding to the volume of the void 235''', to be absent. Otherwise, the core 233''' would tear and generally disintegrate under relatively low loads. The achievement of these functions is independent of the breathability of the absorbent core 233'''. In other words, the void 235''' may or may not produced greater air and vapor transmission through the core 233''' without departing from the scope of the present invention.

As shown in FIG. 6D and in solid lines in FIG. 6E, the scrim 240''' is positioned in the z-direction 25 so that it may be seen in the void 235'''. However as shown in phantom in FIG. 6E, the scrim 240''' may be located higher in the void 235''', or embedded in the material of the absorbent core below the void. Where the scrim 240''' is located in an exposed position within the void 235''', the scrim openings 282''' facilitate passage of liquid into the void 235'''. More than one web of scrim 240''' could be employed in the same absorbent core 233'''.

Figure 6F:
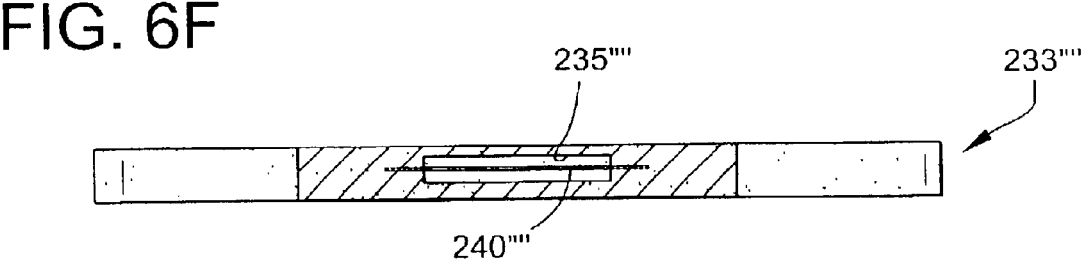
FIG. 6F is a section similar to FIG. 6E, but showing an absorbent core of a fifth modified version.
Figure 6G:
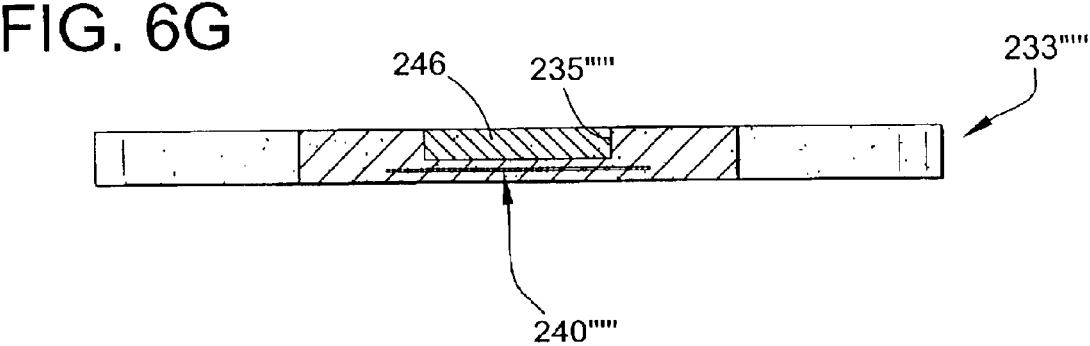
FIG. 6G is a section similar to FIG. 6E, but showing an absorbent core of a sixth modified version.

In another form of the third embodiment shown in FIG. 6F, an absorbent core 233'''' has a void 235'''' which is entirely enclosed within the core. It will be understood that a void (not shown) might also be partially enclosed by the core. This void 235'''' may serve the surge collection function of the void 235''' of FIGS. 6D and 6E. The scrim 240'''' is shown passing through the void 235'''', but may be located at other positions within the thickness of the core 233''''. However, the scrim 240'''' still serves a reinforcing function for the core 233''''. Still another version of the third embodiment shown in FIG. 6G has an absorbent core 233''''' of a substantially similar construction to the core 233'''. However in this instance, void 235'41 '' in the top of the core is filled with a surge member 246. The surge member 246 may be made of conventional surge material or other absorbent material. It will be understood that the surge member 246 may entirely fill the volume of the void 235''''', partially fill it, or have a greater volume so that it extends out from the void. The surge member 246 can facilitate the collection and subsequent absorption of urine into the absorbent core 233'''''. The location of the scrim 240''''' is below the void 235''''', which simplifies the construction, but could be located within the opening.

The reinforcing member may take the form of several components which are unconnected to each other except through their common connection to the absorbent core. For instance, the reinforcing member could be two or more separate webs or pieces of scrim (not shown). For instance, there could be two or more laterally spaced pieces of scrim extending lengthwise of the absorbent core. Another type of reinforcing member is illustrated in FIGS. 7A–7D. The absorbent core is not illustrated in FIGS. 7A–7D for clarity in showing the reinforcing members. The reinforcing members shown in these figures have a reduced resistance to tearing forces in directions lateral of the absorbent core, but are constructed to resist longitudinal tearing forces. For instance, the reinforcing member 340 may take the form of one or more spaced apart strands 380 (broadly, "components") which are unconnected to each other in the absorbent core except through connection with the fibers of the absorbent core. In the version shown in FIG. 7A, the strands 380 each have cross pieces 381 (broadly, "projecting members") attached to the strands at locations spaced along the length of the strands.

Figure 7A:
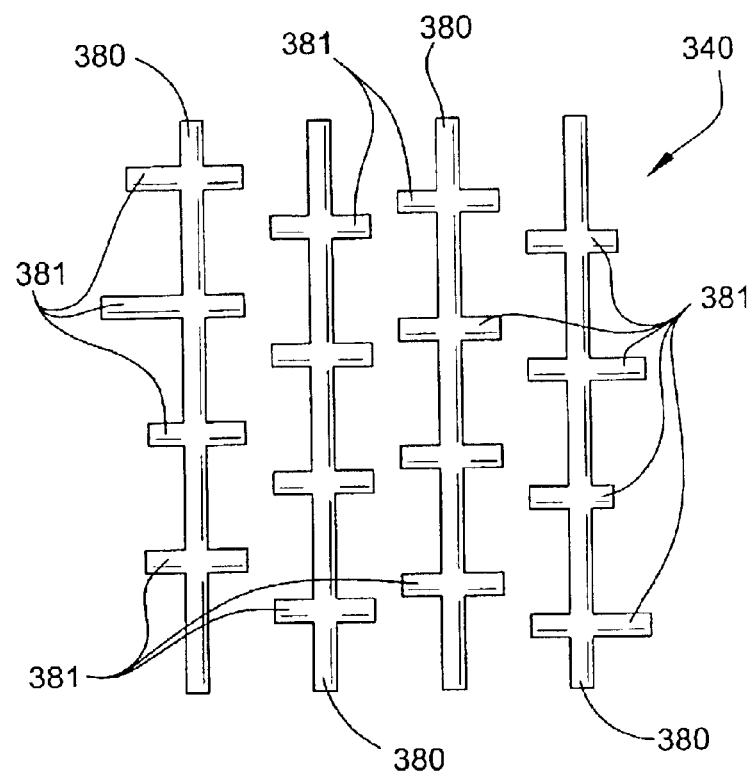
FIG. 7A is a top plan view of a reinforcing member in the form of separate elongate strands having perpendicular cross pieces.
Figure 7B:
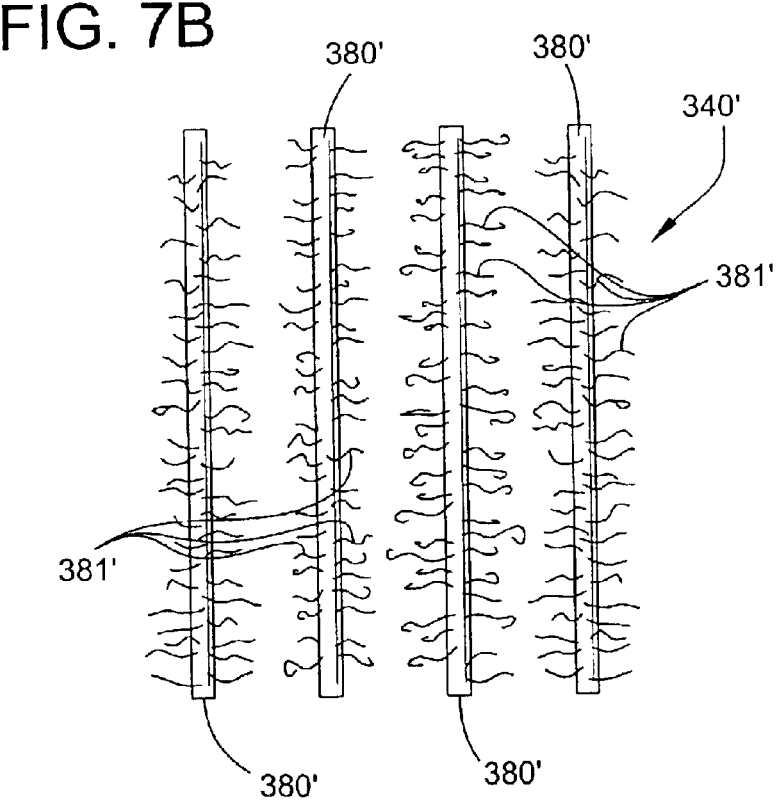
FIG. 7B is a top plan view of a reinforcing member in the form of separate elongate strands having small diameter filaments projecting outwardly therefrom.
Figure 7C:
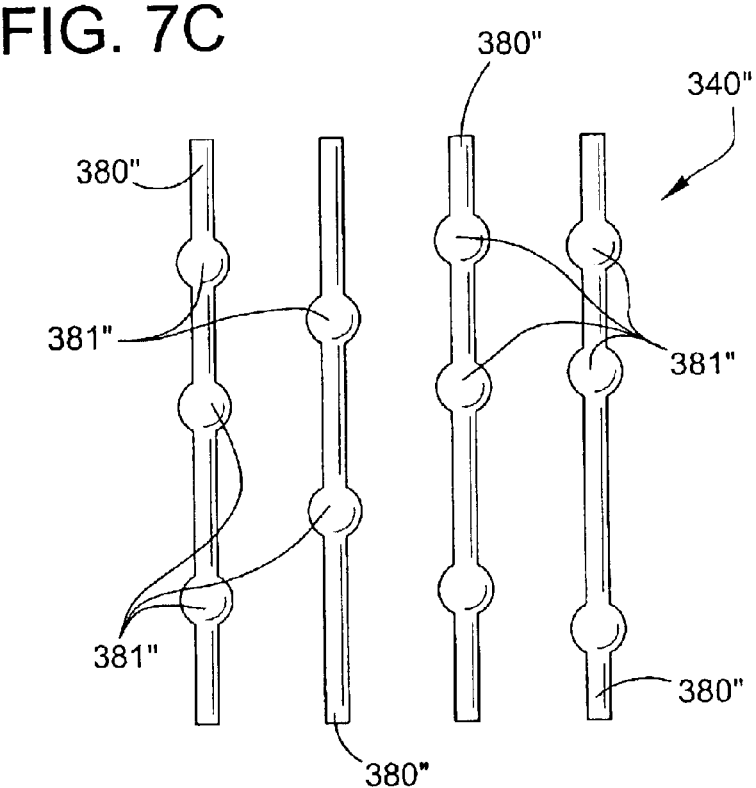
FIG. 7C is a top plan view of a reinforcing member in the form of separate elongate strands having longitudinally spaced knobs thereon.
Figure 7D:
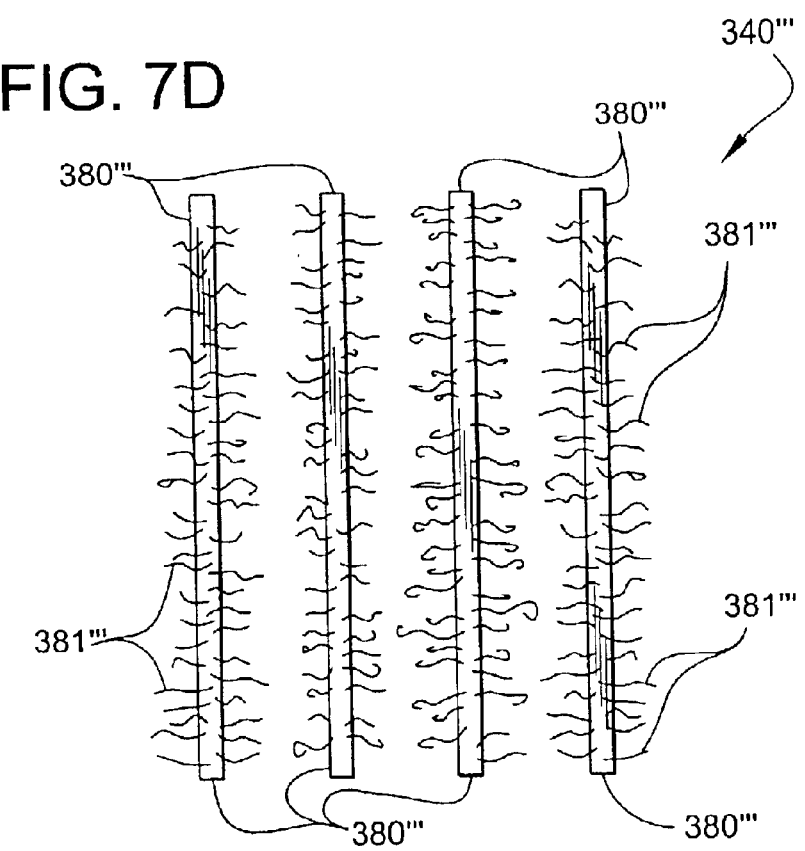
FIG. 7D is a top plan view of a reinforcing member in the form of separate strips of spunbond material.

The cross pieces 381 provide additional locations for the fibers of the absorbent core to be entangled with the reinforcing member 340 so that relative movement of the absorbent core and the strands 380 along the length of the strands is resisted. FIG. 7B shows a reinforcing member 340' in which the cross pieces 381 are replaced by a multiplicity of filaments 381' projecting outward from strands 380'. The filaments 381' would be entangled with the fibers of the absorbent core. In a further version shown in FIG. 7C, a reinforcing member 340'' includes spaced apart strands 380'' having bulbous portions or knobs 381'' located along their length for the same purpose of resisting relative motion between the absorbent core and the strands lengthwise of the core. Still further, FIG. 7D illustrates a reinforcing member 340''' in the form of thin, flat strips 380''' (broadly, "components") of spunbond material. The strips 380''' each have a multiplicity of filaments 381'''extending outwardly from the strip for entanglement with the fibers of the absorbent core. It is to be understood that material other than spunbond material, such as meltblown material, bonded carded web, spunlace, geometric nonwoven apertured fabrics, surge material, or even woven materials such as texturized yarn and combinations and laminations of the foregoing materials, may be used without departing from the scope of the present invention. However, even woven materials, such as textured yarn could be used. Although the cross pieces (or filaments) 381, 381' and 381''' of FIGS. 7A, 7B and 7D are shown spaced from the adjacent strands (380, 380' and 380''') they may overlap the strands and/or each other.

Figure 8:
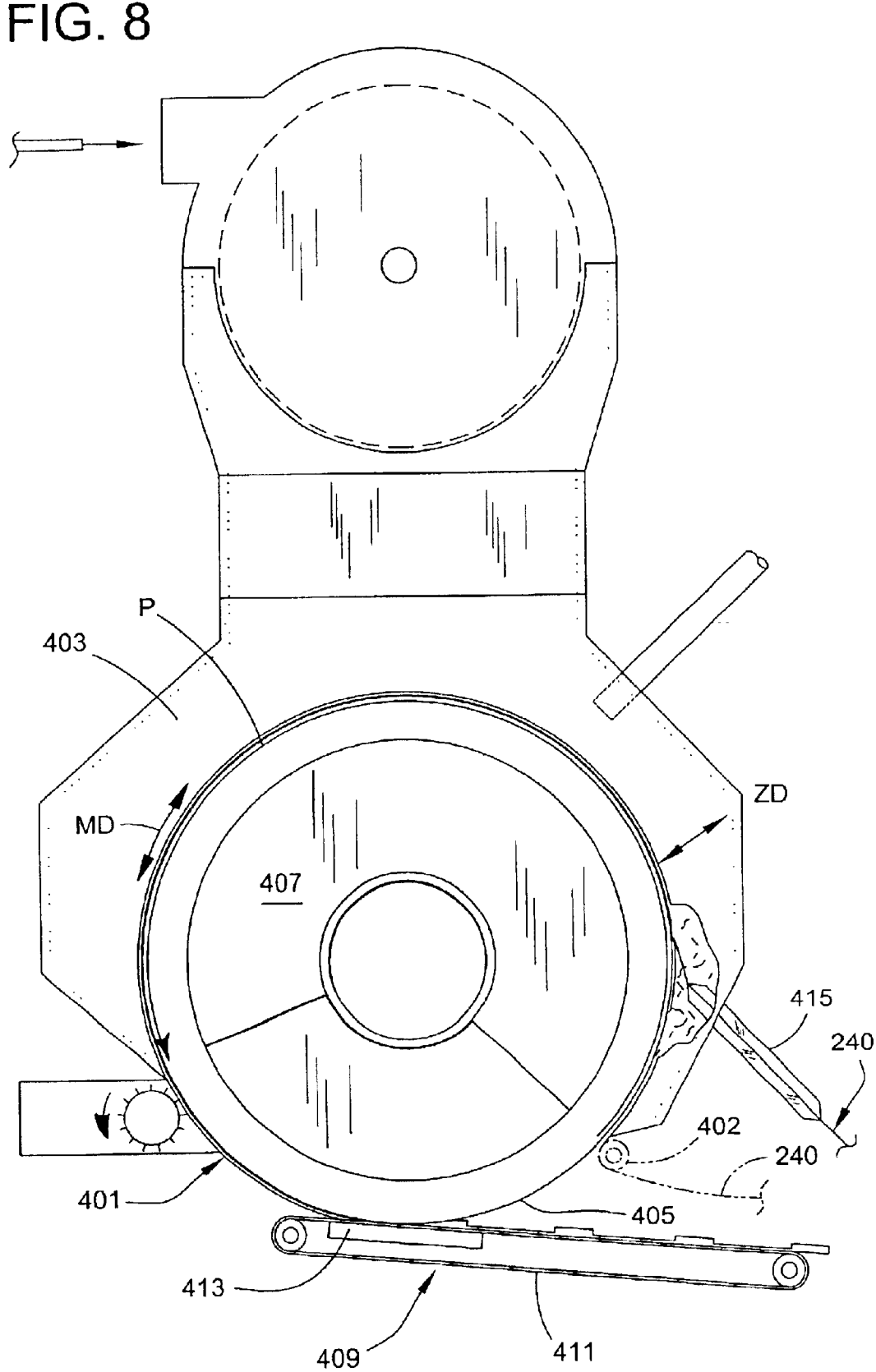
FIG. 8 is a schematic elevation of apparatus for forming an absorbent core.
Figure 9:
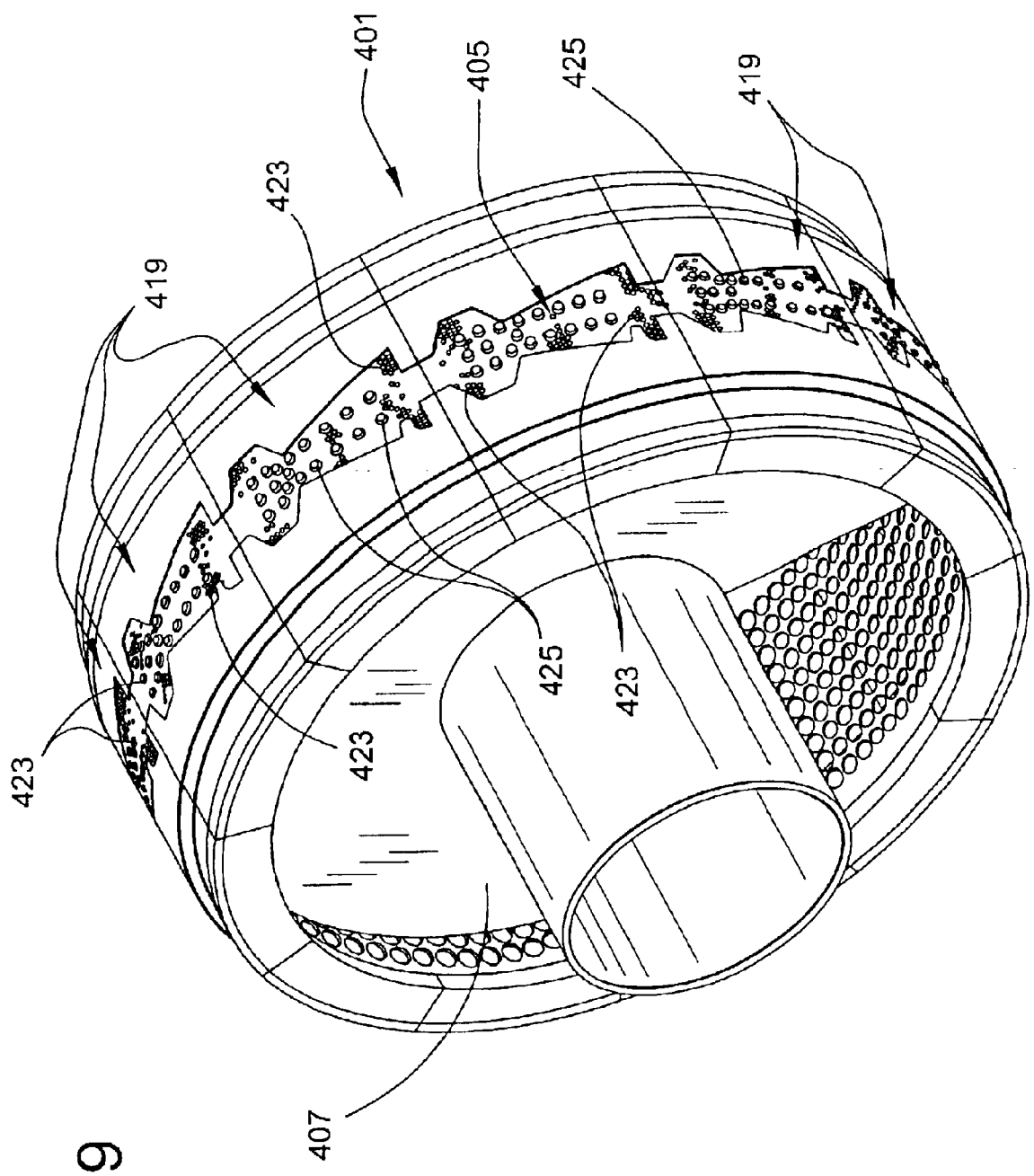
FIG. 9 is a schematic perspective of a forming drum of the apparatus of FIG. 8.

Referring now to FIGS. 8 and 9, apparatus for forming an absorbent core 233 of the third embodiment (or the absorbent cores 233', 233' of the modified third embodiments) is shown to include a forming drum 402. mounted for rotation and received in an open lower end of an air forming chamber vessel 403. The drum 401 includes a foraminous forming surface 405 located on the radially outward facing periphery of the drum. A vacuum duct 407 communicates vacuum pressure to the forming surface 405 for drawing fluidized fibers in an air forming chamber in the vessel 403 onto the forming surface, as the forming surface rotates through the forming chamber over a path P, to build up a fibrous web (which is later cut into individual absorbent cores) having embedded scrim 240. A conveyor 409 located below the drum 401 receives the fibrous web from the drum and carries the web to another location. The conveyor 409 includes a highly air permeable belt 411 and a vacuum chamber 413 under a portion of an upper reach of the belt immediately under the drum 401. Scrim 240 is fed from a roll of scrim (not shown) into the forming chamber vessel 403 through a tube 415 and onto the forming surface 405. Only a general description of the apparatus is given, a more detailed description being found in co-assigned U.S. patent application Ser. No. 10/306,269, entitled PROCESS AND APPARATUS FOR MAKING A REINFORCED FIBROUS ABSORBENT MEMBER, by Venturi no et al. (attorney docket No. 16,836A). Other suitable apparatus is shown and described in co-assigned U.S. patent application Ser. No. 10/305,755 entitled PROCESS AND APPARATUS FOR AIR FORMING AN ARTICLE HAVING A PLURALITY OF REINFORCED SUPERIMPOSED FIBROUS LAYERS by Heyn et al. (attorney docket No. 17,821.1), and U.S. patent application Ser. No. 10/306,186, entitled CONTROLLED PLACEMENT OF A REINFORCING WEB WITHIN A FIBROUS ABSORBENT by Venturino et al. (attorney docket no. 18,613).

Air forming apparatus of this general type, which employs a vacuum to pull fluidized fibers onto a foraminous forming surface mounted on a rotating drum is well known. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference. Other forming drum systems are described in U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001, and U.S. patent application Ser. No. 09/947,128, entitled MULTI-STAGE FORMING DRUM COMMUTATOR by D. P. Murphy et al., filed Sep. 4, 2001 (attorney docket No. 16,632), the entire disclosures of which are incorporated herein by reference. Examples of techniques which can introduce a selected quantity of superabsorbent particles into a forming chamber are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990, the entire disclosure of which is incorporated herein by reference. However, air forming on a flat surface may also be used without departing from the scope of the present invention.

As may be seen in FIG. 9, the forming surface 405 is defined by a multiplicity of forming screens (broadly, "form members"), each designated generally at 419. The forming screens are capable of independent attachment to and removal from the drum 401. However, it is to be understood that the drum 401 could have a single forming screen extending about its circumference without departing from the scope of the present invention. Each forming screen 419 has a foraminous surface through which air readily passes, but on which fibers (and other material) in the forming chamber are deposited to form the fibrous web. Referring now also to FIGS. 10 and 11, each forming screen 419 includes a frame 421 mounting a screen structure 423 which is foraminous, allowing air to pass through, but capturing fibers. Portions of the screen structure 423 are shielded to define the peripheral shape of the absorbent core 233.

The forming screen structure 423 has nubs 425 projecting up from the screen structure. The nubs 425 are not porous so that fibers are generally not deposited on the nubs. Thus, the nubs 425 form the openings 235 in the absorbent core 233. Formation of openings in an absorbent core is known. An example of forming openings using nubs may be found in co-assigned U.S. Pat. No. 6,220,999, entitled METHOD AND APPARATUS FOR FORMING AN APERTURED PAD, by Klugler et al., which issued Apr. 24, 2001, the disclosure of which is incorporated herein by reference.

Figure 12:
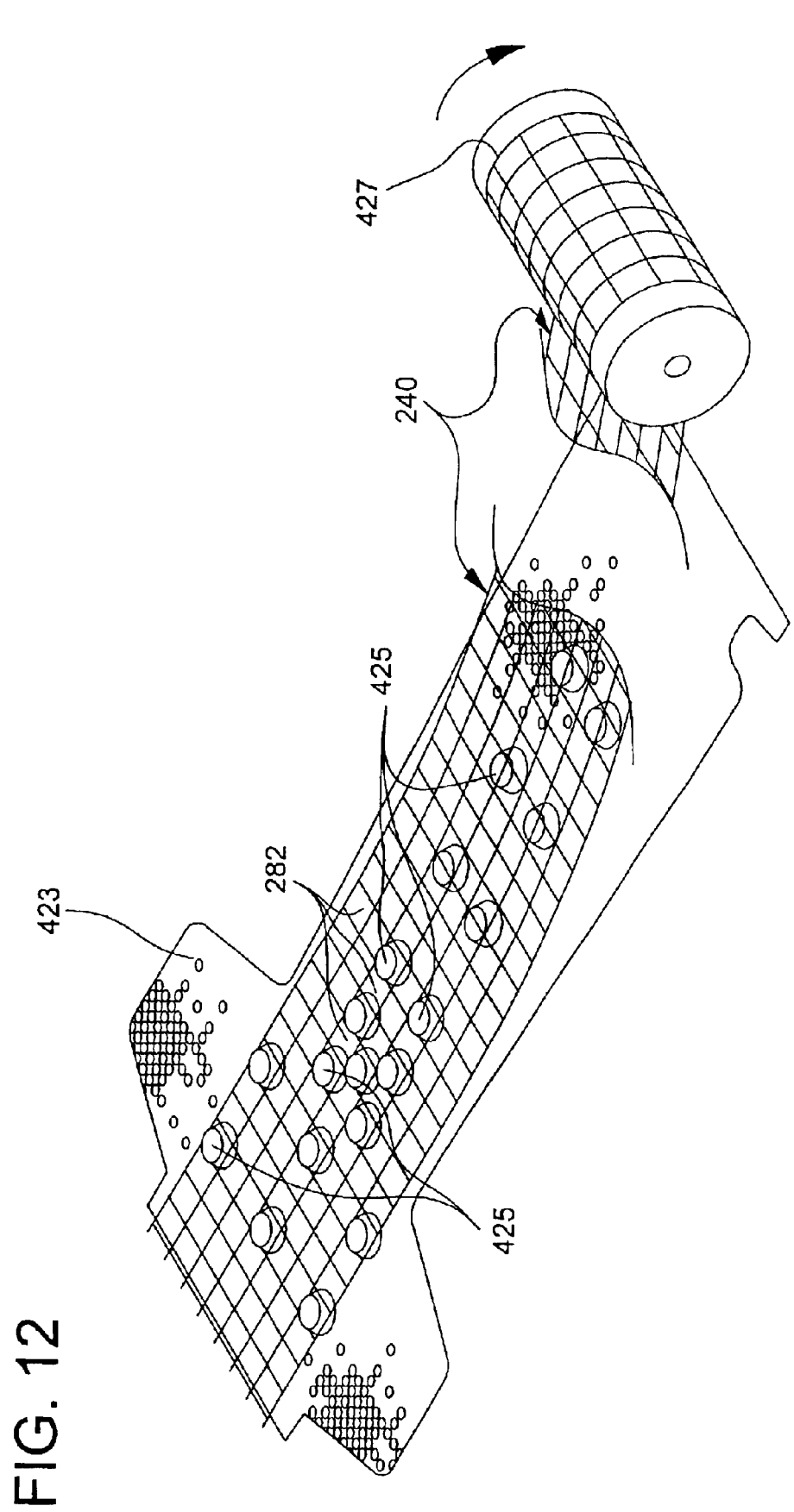
FIG. 12 is a schematic, fragmentary section of the forming screen illustrating the screen receiving the reinforcing member for forming an absorbent core of FIG. 6A.

As shown in FIG. 12, the apparatus includes a feeding device (e.g., a roll 427 of scrim) for feeding the scrim 240 to the forming screen in the forming chamber. In one form of operation, the scrim 240 is guided down onto the screen so that the nubs 425 of the screen structure 423 are received in the openings 282 of the scrim. In this way the openings 235 of the absorbent core 233 are precisely aligned with the openings 282 in the scrim 240. Guiding may be accomplished using guiding equipment such as of the type described in the aforementioned co-assigned U.S. patent application Ser. No. 10/306,269 (Attorney Docket No. 16,836A).

It has been found that fibrous webs air formed to include openings (e.g., openings 235) tend to have a tighter engagement with the forming screen 419 by virtue of engagement of the web with the nubs 425. The presence of the scrim 240 in the fibrous web facilitates release of the fibrous web from the drum 401. The scrim 240 is a continuous web of material, allowing for a continuous peel from the drum 401 even though the absorbent core 233 may be discontinuous. In addition, the scrim 240 provides substantial strength to resist tearing of the fibrous web as forces are applied to remove it from the drum 401 or during other manufacturing operations, such as start up and shut down of the line.

To form the absorbent core 233' of FIG. 6B, the scrim is guided so that junctions where strands 280' of the scrim 240' intersect each other rest on top of the nubs 425. Scrim 240' of a smaller mesh size (i.e., smaller than the diameter of the nubs 425 at their upper ends) is used. The smaller mesh size helps to assure that the nubs 425 will not be received in the openings 282' of the scrim 240' so that the scrim will rest on top of the nubs. The manufacture of such an absorbent core 233' is illustrated schematically in FIG. 13. It is to be understood that the junctions may rest anywhere on the nubs 425, not necessarily in the center, as shown.

Figure 13:
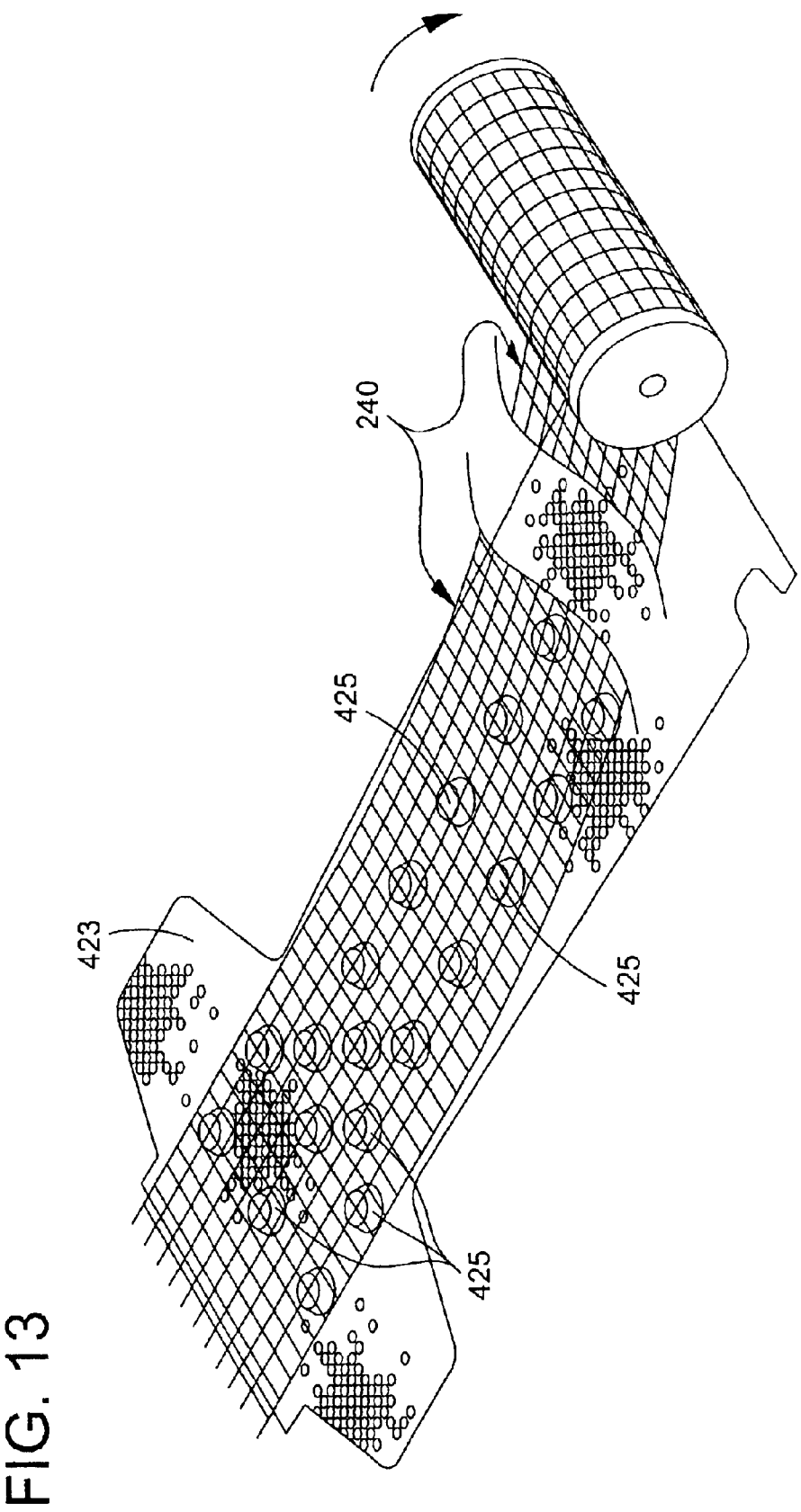
FIG. 13 is a schematic, fragmentary section of the forming screen illustrating the screen receiving the reinforcing member for forming an absorbent core of FIG. 6B.

The nubs 425 can be beneficially used to locate the scrim 240, 240' in the thickness or z-direction of the core 233, 233'. The scrim 240' may rest on top of the nubs 425 as shown in FIG. 13, or scrim 240 may fit part way down on the nubs as shown in FIG. 12. In either case, the z position of the scrim is established by the nubs 425. Among other advantages, this allows the scrim 240 to be placed on the forming surface 405 prior to entry of the forming surface into the forming chamber vessel 403. As shown in phantom in FIG. 8, the scrim 240 may be fed over a guide roll 402 onto the forming surface 405 prior to entry into the forming chamber 403. It is not necessary for a layer of fluff ("fluidized fibers") to be deposited on the forming surface 405 prior to the scrim (240, 240') because the fluff is not needed to space the scrim off of the bottom of the forming surface. Thus, for example, the tube 415 could be eliminated. In general, the scrim might be placed on the forming surface 405 at locations ranging from prior to entering the forming chamber vessel 403 to a location about 25% of the way along the path P from an entrance of the forming chamber (i.e., from the location where the forming surface 405 passes into the forming chamber 403). In another embodiment, the scrim 240 is placed on the forming surface 405 at a location about 15% of the way along the path P from the entrance of the forming chamber vessel.

Figure 14A:
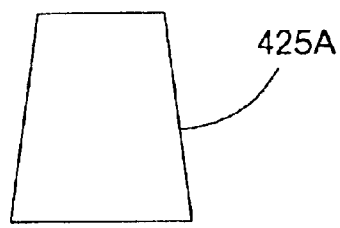
FIGS. 14A–14F are schematic illustrations of forming nubs for forming screens.
Figure 14B:
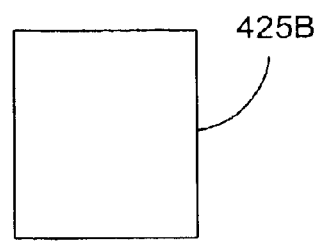
Figure 14C:
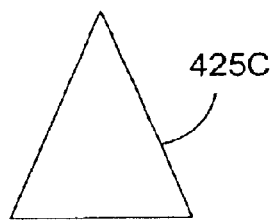
Figure 14D:
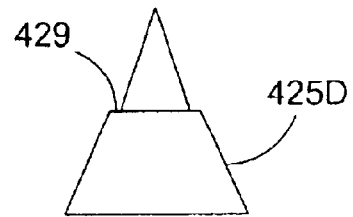
Figure 14E:
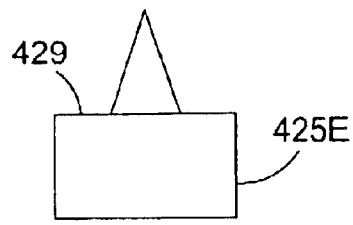

The nubs may have different configurations, some of which are illustrated in FIGS. 14A–14F. In FIG. 14A, the nub 425A may be sized slightly larger than the scrim opening 282 so that although the nub is received in the scrim opening, an interference fit holds the scrim 240 in position above the bottom of the nub and above the foraminous surface. FIGS. 14A and 14C show nubs 425A, 425C which taper toward their free ends to facilitate starting the scrim opening 282 on the nubs. The tapered nubs 425A, 425C also promote release of the fibrous web from the forming surface 405 by providing a release angle. The scrim 240 moves down on the nub 425A, 425C until the nub diameter is the same or slightly larger than the opening 282 of the scrim. The tapered nubs 425D, 425E of FIGS. 14D and 14E are similar, but have shoulders 429 which engage and positively locate the scrim at a fixed height. By manipulation of the height and width of the nubs 425D, 425E (and locations of the shoulders 429) the location of the scrim in the thickness or z-direction 25 can be selected. It is also envisioned that by making the nubs 425 sufficiently short, the openings 235 would not extend completely through the absorbent core 233, leaving rather instead dimples (e.g., dimple 235" of FIG. 6C) in one face of the absorbent core.

Figure 14F:
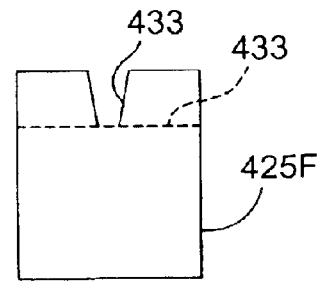

The nubs 425A, 425, 425F shown in FIGS. 14A, 14B and 14F are useful in forming the absorbent cores 233', 233" of the modified third embodiments (FIGS. 6B and 6C). Although the nubs 425A–425F illustrated are generally symmetrical, the nubs may have other, symmetrical and nonsymmetrical shapes. To form the modified absorbent core 233', 233" where the junction of intersecting strands 280', 280" of the scrim 240' are located in the openings 235', or dimples 235" of the core, the scrim is located in the forming chamber on top of the nubs. The nub 425F of FIG. 14F is formed with a pair of crossing, flared grooves 433 in its top surface for receiving strands 280', 280" at a junction to more positively locate the strands on the top of the nub. The flaring of the grooves 433 facilitates capturing and centering the strands 280', 280" in the groove. However, where scrim openings 82 are small, the grooves 433 are not needed. Moreover, it is not necessary in that event to precisely control the placement of the scrim 40 as it is being placed onto the forming surface 405.

Referring once more to FIGS. 1 and 2, to improve the containment of the high-absorbency material, absorbent structure 32 can include an overwrap, such as a wrap sheet 74, which is placed immediately adjacent and around the absorbent core 33 and may be bonded to the absorbent core and to the various other components of the diaper 10 (FIG. 2). The wrap sheet 74 is preferably a layer of absorbent material which covers the major bodyside and outerside surfaces of the absorbent core 33, and preferably encloses substantially all of the peripheral edges of the absorbent core to form a substantially complete envelope thereabout. Alternatively, the wrap sheet 74 can provide an absorbent wrapping which covers the major bodyside and outerside surfaces of the absorbent core 33, and encloses substantially only the lateral side edges of the absorbent core. Accordingly, both the linear and the inwardly curved portions of the lateral side edges of the wrap sheet 74 can be closed about the absorbent core. In such an arrangement, however, the end edges of the wrap sheet 74 may not be completely closed around the end edges of the absorbent core 33 at the waistband regions of the article. For example, the complete wrap sheet 74, or at least the bodyside layer of the wrap sheet, may comprise a meltblown web composed of meltblown fibers, such as meltblown polypropylene fibers. Another example of the absorbent wrap 74 may comprise a low porosity cellulosic web, such as a tissue composed of an approximately $^{50}/_{50}$ blend of hardwood/softwood fibers.

The absorbent wrap 74 may comprise a multi-element wrapsheet which includes a separate bodyside wrap layer and a separate outerside wrap layer, each of which extends past all or some of the peripheral edges of the absorbent core 33. Such a configuration of the wrap sheet can, for example, facilitate the formation of a substantially complete sealing and closure around the peripheral edges of the absorbent core 33. In the back waistband portion of the illustrated diaper, the absorbent wrap 74 may also be configured to extend an increased distance away from the periphery of the absorbent core to add opacity and strength to the back side-sections of the diaper 10. In the illustrated embodiment, the bodyside and outerside layers of the absorbent wrap 74 can extend at least about ½ inch beyond the peripheral edges of the absorbent structure to provide an outwardly protruding, flange-type bonding area over which the periphery of the bodyside portion of the absorbent wrap may be completely or partially connected to the periphery of the outerside portion of the absorbent wrap.

The bodyside and outerside layers of the wrap sheet 74 may be composed of substantially the same material, or may be composed of different materials. For example, the outerside layer of the wrap sheet 74 may be composed of a relatively lower basis weight material having a relatively high porosity, such as a wet strength cellulosic tissue composed of softwood pulp. The bodyside layer of the wrap sheet 74 may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

In desired arrangements, a spacer layer 76 may be interposed between the absorbent structure 32 and the backsheet component 30 to provide desired benefits. Where the backsheet 30 is vapor permeable, for example, the spacer layer 76 can operatively locate and separate the backsheet 30 away from the absorbent structure 32 by a discrete distance. The resultant spacing distance can help to reduce a damp or cool feeling that may arise when the absorbent becomes wetted. In one embodiment, the spacer layer comprises a hydrophobic, nonwoven material having a thickness of at least about 0.10 centimeters, and a basis weight of from about 20 to about 120 grams per square meter.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent structure for absorbing liquid in an absorbent article, the absorbent structure comprising an absorbent member made at least in part of an absorbent material, the absorbent member having at least one zone therein having a higher air permeability than an adjacent lower air permeability cone of the absorbent member, and a reinforcing member at least partially embedded in the absorbent member for reinforcing the absorbent member to hold its configuration under loads experienced by the absorbent structure.

2. An absorbent structure as set forth in claim 1 wherein the reinforcing member is adapted for passage of liquid through the reinforcing member.

3. An absorbent structure as set forth in claim 2 wherein the reinforcing member comprises a sheet of lofty nonwoven material.

4. An absorbent structure as set forth in claim 2 wherein the reinforcing member has openings therein for the passage of liquid.

5. An absorbent structure as set forth in claim 4 wherein the absorbent member has multiple higher air permeability zones, each higher air permeability zone comprising a passage in the absorbent member for passing air through the absorbent member, the passages of the absorbent member being out of registration with the openings of the reinforcing member.

6. An absorbent structure as set forth in claim 5 wherein a portion of the reinforcing member is exposed in at least some of the passages in the absorbent member.

7. An absorbent structure as set forth in claim 4 wherein the absorbent member has multiple higher air permeability zones, each higher air permeability zone comprising a passage in the absorbent member for passing air through the absorbent member, at least some of the passages of the absorbent member being in registration with the openings of the reinforcing member such that no portion of the reinforcing member is exposed in said at least some of the passages in the absorbent member.

8. An absorbent structure as set forth in claim 4 wherein the reinforcing member comprises strands arranged in a pattern in which at least some of the strands intersect one another at junctions, the strands being joined together where they intersect each other.

9. An absorbent structure as set forth in claim 8 wherein some of the strands extend generally lengthwise of the absorbent structure and some of the strands extend generally widthwise of the absorbent structure.

10. An absorbent structure as set forth in claim 9 wherein the absorbent member has multiple higher air permeability zones, each higher air permeability zone comprising a passage in the absorbent member for passing air through the absorbent member, the passages of the absorbent member being out of registration with the openings of the reinforcing member such that at least two longitudinally extending strands or at least two laterally extending strands are exposed in at least some of the passages.

11. An absorbent structure as set forth in claim 1 wherein the absorbent member has a length and a width, and wherein no portion of the reinforcing member projects laterally outwardly of the absorbent member.

12. An absorbent structure as set forth in claim 11 wherein no portion of the reinforcing member is exposed outside a perimeter of the absorbent member.

13. An absorbent structure as set forth in claim 1 wherein each higher air permeability zone comprises a passage in the absorbent member, at least portions of the absorbent member being spaced apart from each other across the passage.

14. An absorbent structure as set forth in claim 13 wherein the absorbent member comprises at least two distinct, spaced apart sections of absorbent material, and wherein the passage defines a gap spacing apart the at least two absorbent member sections, the absorbent material of each section being free of contact with the absorbent material of the other section, the reinforcing member bridging the gap for interconnecting the sections.

15. An absorbent structure as set forth in claim 14 wherein the absorbent member sections extend lengthwise of the absorbent structure, the gap spacing the absorbent member sections laterally of each other.

16. An absorbent structure as set forth in claim 14 wherein the absorbent member sections extend widthwise of the absorbent structure, the gap spacing the absorbent member sections lengthwise of the absorbent structure.

17. An absorbent structure as set forth in claim 13 wherein the absorbent member comprises multiple passages.

18. An absorbent structure as set forth in claim 17 wherein each passage extends through the absorbent member and opens on generally opposite sides of the absorbent member.

19. An absorbent member as set forth in claim 1 wherein said at least one zone of higher air permeability comprises a lower basis weight region of the absorbent member.

20. An absorbent member as set forth in claim 19 wherein each lower basis weight region comprises a dimple extending inwardly from one major surface of the absorbent member.

21. An absorbent structure as set forth in claim 1 wherein the reinforcing member comprises spaced apart components unconnected to each other except through connection with the absorbent member.

22. An absorbent structure as set forth in claim 21 wherein each component has projecting elements extending outwardly therefrom.

23. An absorbent structure as set forth in claim 22 wherein each projecting element comprises a multiplicity of filaments.

24. An absorbent structure as set forth in claim 22 wherein each projecting element comprises a cross piece arranged generally perpendicularly to the component.

25. An absorbent structure as set forth in claim 22 wherein each projecting element comprises a knob.

26. An absorbent structure as set forth in claim 1 wherein said at least one higher air permeability zone forms about 5% to 75% of the area of at least one major surface of the absorbent structure.

27. An absorbent article adapted to be worn by a wearer for absorbing body exudates, the absorbent article comprising a liquid permeable liner, a backsheet layer and an absorbent structure as set forth in claim 1.

28. An absorbent article as set forth in claim 27 having a skin hydration value of less than about 18 grams per square meter per hour.

29. An absorbent article as set forth in claim 28 having a skin hydration value of less than about 15 grams per square meter per hour.

30. An absorbent article as set forth in claim 27 further comprising a spacer layer comprising a hydrophobic, nonwoven material having a thickness of at least about 0.10 centimeters and a basis weight of from about 20 to about 120 grams per square meter.

31. An absorbent article as set forth in claim 27 further comprising a surge management layer located between the liner and backsheet layer, the surge management layer comprising a nonwoven material having a basis weight of from 5 about 20 to about 300 grams per square meter.

32. An absorbent structure for absorbing liquid in an absorbent article, the absorbent structure comprising an absorbent member made at least in part of an absorbent material, the absorbent member having at least one void defined therein, at least some absorbent material of the absorbent member being spaced apart across said void, and a reinforcing member at least partially embedded in the absorbent member for reinforcing the absorbent member to maintain its integrity under loads experienced by the absorbent structure.

33. An absorbent structure as set forth in claim 32 wherein the void defines a liquid collection volume for collecting a volume of liquid applied rapidly to the absorbent structure for subsequent absorption into the absorbent member.

34. An absorbent structure as set forth in claim 32 wherein the reinforcing member is at least partially in registration with the void.

35. An absorbent structure as set forth in claim 34 wherein the reinforcing member extends through the void.

36. An absorbent structure as set forth in claim 34 wherein the reinforcing member is entirely embedded within the absorbent member.

37. An absorbent structure as set forth in claim 32 wherein the void is enclosed within the absorbent member.

38. An absorbent structure as set forth in claim 32 wherein the void opens outwardly of the absorbent member on one side thereof.

39. An absorbent structure as set forth in claim 32 further comprising a surge member located at least partially in the void.

40. An absorbent structure as set forth in claim 39 wherein the surge member substantially fills the void.

41. An absorbent structure for absorbing liquid in an absorbent article, the absorbent structure comprising an absorbent member made at least in part of an absorbent material, the absorbent member having at least one zone therein having a higher air permeability than an adjacent lower air permeability zone of the absorbent member, and a reinforcing member for reinforcing the absorbent member to hold its configuration under loads experienced by the absorbent structure, the reinforcing member having an inner face and an outer face, at least a portion of the reinforcing member being secured within the absorbent member with the inner face and the outer face of the reinforcing member at said portion thereof being substantially overlaid by the absorbent member.

* * * * *

UNITED STATES PATENT AND TRADEMARK OFFICE
CERTIFICATE OF CORRECTION

PATENT NO. : 6,802,834 B2
DATED : October 12, 2004
INVENTOR(S) : Shannon K. Melius et al.

It is certified that error appears in the above-identified patent and that said Letters Patent is hereby corrected as shown below:

Column 7,
Line 28, "some bonding" should read -- sonic bonding --.

Column 13,
Line 19, "MAINTIAINS" should read -- MAINTAINS --.

Column 17,
Line 39, "235' 4T" should read -- 235"" --.

Column 18,
Line 37, "402" should read -- 401 --.

Column 22,
Line 47, "cone" should read -- zone --.

Column 24,
Line 37, should read -- from about 20 to about 300 grams --.

Signed and Sealed this

Twenty-eighth Day of March, 2006

JON W. DUDAS
*Director of the United States Patent and Trademark Office*